[19] United States Patent
Song et al.

[11] Patent Number: 5,567,302
[45] Date of Patent: Oct. 22, 1996

[54] ELECTROCHEMICAL SYSTEM FOR RAPID DETECTION OF BIOCHEMICAL AGENTS THAT CATALYZE A REDOX POTENTIAL CHANGE

[75] Inventors: Herking Song, Fremont; Dean G. Hafeman, Hillsborough, both of Calif.

[73] Assignee: Molecular Devices Corporation, Sunnyvale, Calif.

[21] Appl. No.: 483,249

[22] Filed: Jun. 7, 1995

[51] Int. Cl.$^6$ .................................................. G01N 27/26
[52] U.S. Cl. ........................ 205/777.5; 204/403; 204/406; 204/412; 204/418; 422/68.1; 422/82.01; 422/82.03; 435/4; 435/29; 435/817; 435/287.1
[58] Field of Search ........................ 205/777.5; 204/418, 204/403, 406, 412; 422/82.01, 82.03, 68.1; 435/4, 817, 29, 288, 291

[56] References Cited

U.S. PATENT DOCUMENTS

| | | | |
|---|---|---|---|
| 4,488,780 | 12/1984 | Nicholson | 350/320 |
| 4,591,550 | 5/1986 | Hafeman et al. | 435/4 |
| 4,942,127 | 7/1990 | Wada et al. | 435/11 |
| 4,963,815 | 10/1990 | Hafeman | 324/715 |
| 5,089,391 | 2/1992 | Buechler et al. | 435/7.1 |
| 5,108,893 | 4/1992 | Baret | 435/6 |
| 5,229,073 | 7/1993 | Luo et al. | 422/56 |
| 5,468,605 | 11/1995 | Harris et al. | 435/4 |
| 5,482,830 | 1/1996 | Bogart et al. | 435/5 |

OTHER PUBLICATIONS

J. Briggs and P. R. Panfili, *Analytical Chemistry*, 83, 850–859, 1991.

Sheldon, E. L., Nagainis, P. A. and Kung, V. T.: Detection of Total DNA with Single–Stranded DNA Binding Portein Conjugates. *Biochem. and Biophys. Res. Comm.* 165:474–480 (1989) no month available.

Kung, V. T., Panfili, P. R., Sheldon, E. L., King, R. S., Nagainis, P. A., Gomez, B., Ross, D. A. Briggs, J., and Zuk, R. F.: Picogram Quantitation of Total DNA Using DNA–Binding Proteins in a Silicon Sensor–Based System. *Anal. Biochem.* 187:220–227 (1990) no month available.

Olson, J. D., Panfili, P. R. Armenta, R., Femmel, M., Merrick, H., Gumperz, J., Goltz, M., and Zuk, R. F.: A Silicon Sensor–Based Filtration Immunoassay Using Biotin––Mediated Capture. *J. Immunological Methods* 134: 71–79 (1990) no month available.

Hafeman, D. G., Parce, J. W., and McConnell, H. M.: Light–Addressable Potentiometric Sensor for Biochemical Systems. *Science* 240:1182–1185 (1988) no month available.

(List continued on next page.)

*Primary Examiner*—Bruce F. Bell
*Attorney, Agent, or Firm*—Banner & Allegretti, Ltd.

[57] ABSTRACT

The present invention relates to a system for detecting, in a reliable, precise and highly sensitive manner, biochemical agents such as enzymes that catalyze a redox potential change. One electrode is used to measure redox potential changes in an aqueous electrolyte containing the biochemical agents. Another electrode is used to deliver a feedback current to the electrolyte in response to measured Changes in electrolyte redox potential. The amount of feedback current or charge delivered through the electrode to the electrolyte is sufficient in magnitude to maintain a constant redox potential. Quantitation of the amount of feedback current or charge necessary to maintain the constant redox potential may then be used to determine the amount of biochemical agents present. Alternatively, the redox potential need not be kept constant, but instead may be allowed to reach a new steady-state. Thus, the current, or charge, conducted by a feedback electrode to maintain a new steady-state potential in the presence of an enzymatic reaction may be used to quantitate the amount of enzymatic activity present. The present invention provides precision in the quantitation results, high sensitivity in the enzyme detection, and a wider dynamic range for quantitation of the biochemical agent.

20 Claims, 24 Drawing Sheets

OTHER PUBLICATIONS

Bousse, L., Kirk, G., and Signal, G.: Biosensors for Detection of Enzymes Immobilized in Microvolume Reaction Chambers. *Sensors and Actuators* B1:555–560 (1990) no month available.

Libby, J. M., and Wada, H. G.: Detection of *Neisseria meningitidis* and *Yersinia pestis* with a Novel Silicon–Based Sensor. J. Clin. Micro. 27:7:1456–1459 (1989) no month available.

Sigal, G. B., Hafeman, D. G., Parce, J. W., and McConnell, H. M. Electrical Properties of Phospholipid Bilayer Membranes Measured with a Light–Addressable Potentiometric Sensor. In: ACS Symposium Series 403, *Chemical Sensors and MicroInstrumentation* (R. W. Murray, R. E. Dessy, W. R. Heineman, J. Janata, and W. R. Seitz, Eds.) American Chemical Society, Washington, DC (1989) pp. 46–64 no month available.

Briggs, J., Kung, V. T., Gomez, B., Kasper, K. C., Nagainis, P. A., Masino, R. S., Rice, L. S., Zuk, R. F., and Ghazarossian, V. E. Sub–Femtomole Quantitation of Proteins with Threshold®, for the Biopharmaceutical Industry. *Biotechniques* 9, 598–606 (1990) no month available.

Bergveld, P. The Significance of Feedback Control for Chemical Sensors. *Sensors and Actuators* B 8: 47–52 (1992) no month available.

Bousse, L. Owicki, J. C., and Parce, J. W. Biosensors with Microvolume Reaction Chambers. In: *Chemical Sensor Technology* vol. 4, (Yamauchi, S., Ed.) Kodansha Ltd., Tokyo and Elsevier, Amsterdam (1992), pp. 148–166 no month available.

Lundström, I., Erlandsson, R., Frykman, U., Hedborg, E., Spetz, A., Sundgren, H., Welln, S., Winquist, F., Artificial 'olfactory' images from a chemical sensor using a light-pulse technique. *Nature*, vol. 352, (1991) no month available.

ELECTROCHEMICAL SYSTEM FOR RAPID DETECTION OF BIOCHEMICAL AGENTS THAT CATALYZE A REDOX POTENTIAL CHANGE

BACKGROUND OF THE INVENTION

This invention relates to a reliable, precise, and highly sensitive analytical system for detecting biochemical agents that catalyze a redox potential change.

By way of background, a light-addressable potentiometric sensor ("LAPS") and a rapid capture immunoassay system have been developed by the Molecular Devices Corporation of Sunnyvale, Calif. The rapid capture immunoassay system, which is commercially available under the Threshold® trademark, uses LAPS technology to perform a multiplicity of pH-based immunoassays in small volumes with high sensitivity. In addition to the detection and quantitation of hydrogen ions, specific ion-sensing membranes may be deposited to fabricate sensing sites to detect and quantitate several other basic analytes including, for example, aqueous ions such as $Na^+$, $K^+$, $Ca^{++}$, and $Cl^-$. Deposition of a valinomycin-containing polyvinyl-chloride membrane results in a spatially-resolved, $K^+$ion sensor. Various gases, including hydrogen, ammonia, hydrogen sulfide, ethylene and ethanol, can also be detected and quantitated. Multiple assays of a single basic analyte, or of several basic analytes, may be monitored simultaneously at a multiplicity of sites on a single dielectric-coated semiconductor surface of the LAPS device.

In the small volume detection chamber of the Threshold® immunoassay detection system, the lower limit of detection of pH-altering enzymes is determined by the surface pH-buffer capacity, pH-buffer concentration, and the volume of the reaction chamber. A nitrocellulose membrane is utilized to specifically capture analyte molecules which are then labeled with an enzyme capable of catalyzing a pH-changing reaction. One limitation to the sensitivity for detection of such enzymes is the fact that the nitrocellulose membrane itself has a fixed site buffer capacity equivalent to 2.3 mM buffer concentration. Impurities retained on the membrane from samples tend to further increase the buffer capacity. A sensitivity limitation of the Threshold® Immunoassay System is that proteinaceous materials adsorbed onto the membrane from samples tend to have many proton-dissociable sites. Therefore, it is difficult to reliably improve sensitivity by reducing the surface pH-buffer capacity of the membrane.

The LAPS device can also be configured to monitor redox potential. Multiple, spatially separate, redox potential measurements can be made by depositing thin pads of metallic gold (or other noble metal) on the dielectric. When the electrolyte solution contains a redox pair such as ferricyanide-ferrocyanide, the potential of the nobel metal is determined by the standard redox potential of the redox pair and the ratio of activities of the members of the redox pair in accordance with the Nernst equation. Intensity-modulated illumination of a region of semiconductor adjacent the nobel metal produces an alternating photocurrent similar to that observed with the pH-sensing device. In this case, however, the relationship between the measured alternating photocurrent, I, and the applied bias potential, $\Psi$, responds to changes in redox potential of the electrolyte.

The Threshold® immunoassay detection system has been modified to quantitate enzymes that generate redox-active products. The modified Threshold® systems use the LAPS device, modified to monitor redox potential, as well as selected pairs of enzyme substrate and soluble redox mediators to provide sensitive detection and quantitation of enzymes such as alkaline phosphatase (ALP) and horseradish peroxidase (HRP). The enzyme substrate is chosen to react rapidly in the presence of the enzyme and to generate a redox active product. The soluble redox mediator functions to react with the redox-active product and carry electrons to or from a metal electrode or the metallic gold pads on the LAPS device.

The Threshold® immunoassay detection system modified to detect redox potential may have a higher sensitivity for detection of small quantities of enzyme provided that the redox buffer capacity on the nitrocellulose membrane is lower than the pH-buffering capacity. Sensitivity could also be improved by decreasing the volume of the reaction chamber. Decreasing the volume of the reaction chamber to a very small volume, however, makes it difficult to precisely maintain a constant volume during repetitive measurements. Because the measured rate of change in potential is inversely proportional to volume and directly proportional to the amount of enzyme present, precise determination of the quantity of enzyme requires precise control of volume. Such control, however, become increasingly difficult as the micro-volume becomes vanishingly small.

One way to overcome this limitation is to make the enzyme quantitation independent of volume by providing a feedback current by means of a feedback electrode to keep the redox potential constant. In this way, the amount of feedback current required to maintain the potential constant may be measured and, in turn, used to determine the amount of enzyme or enzymatic activity present. Alternatively, the redox potential need not be kept constant, but instead may be allowed to reach a new steady-state. Thus, the current, or charge, conducted by a feedback electrode to maintain a new steady-state potential in the presence of an enzymatic reaction may be used to quantitate the amount of eneymatic activity present.

SUMMARY OF THE INVENTION

The present invention provides a solution to the micro-volume control problem described above. A coulometric feedback system is employed to maintain the electrolyte microvolume at a constant redox potential. A coulometric feedback system may consist of, for example, a LAPS device, described above, with an additional feedback electrode array. The LAPS device may be placed in contact with one side of the thin capture membrane and the feedback electrode array placed in contact with the opposite side. The LAPS device thereby monitors the redox potential of each site, and the feedback electrode array injects the appropriate charge necessary to maintain a constant, or steady-state, redox potential. Enzymes such as β-D-galactosidase, horseradish peroxidase, alkaline phosphatase, or glucose oxidase, are thus quantitated by recording the total amount of feedback charge injected over a predetermined injection period, in order to maintain the constant or substantially steady-state conditions.

Compared with a strictly potentiometric LAPS redox mode technology, the coulometric feedback system can be used to more precisely quantitize the amount of enzyme activity present. More particularly, precise control of the micro-volume is not required with the coulometric feedback system. The coulometric feedback system therefore has greater analytical precision insofar as the precision of enzyme quantitation is no longer affected by the assay volume.

In addition, measurement of redox potential changes has been shown to be about 100-fold more sensitive for the detection of enzyme molecules compared to measurement of pH changes. This is because the capture membrane has a much lower redox buffering capacity than pH buffering capacity. Moreover, a smaller assay volume may be monitored without sacrificing the precision of the results.

Further, a wider dynamic range for quantitation of the enzyme can be obtained with the coulometric feedback system because the feedback system is able to counteract the change in chemical potential caused by high concentrations of enzyme in the micro-volume. In particular, the redox mediator consumed by the enzymatic reaction is continuously regenerated by the feedback system of the present invention.

It is therefore an object of the invention to improve the precision of analytical results from biochemical detection methodology.

It is also an object of the invention to provide more sensitive biochemical detection methodology.

It is also an object of the invention to provide a wider dynamic range for quantitation of biochemical agents that catalyze a redox potential change.

It is also an object of the invention to provide reagent systems to carry out the coulometric feedback method of detection.

It is also an object of the invention to provide a biochemical detection and quantitation system having excellent electrochemical properties, such as reversible electrochemical behavior and fast kinetics.

Further objects and advantages of the present invention will become apparent in the following description.

BRIEF DESCRIPTION OF THE DRAWINGS

There is shown in the drawing presently preferred embodiments of the present invention, wherein like numerals in the various views refer to like elements and wherein.

DESCRIPTION OF THE PREFERRED EMBODIMENTS

Figure 1:
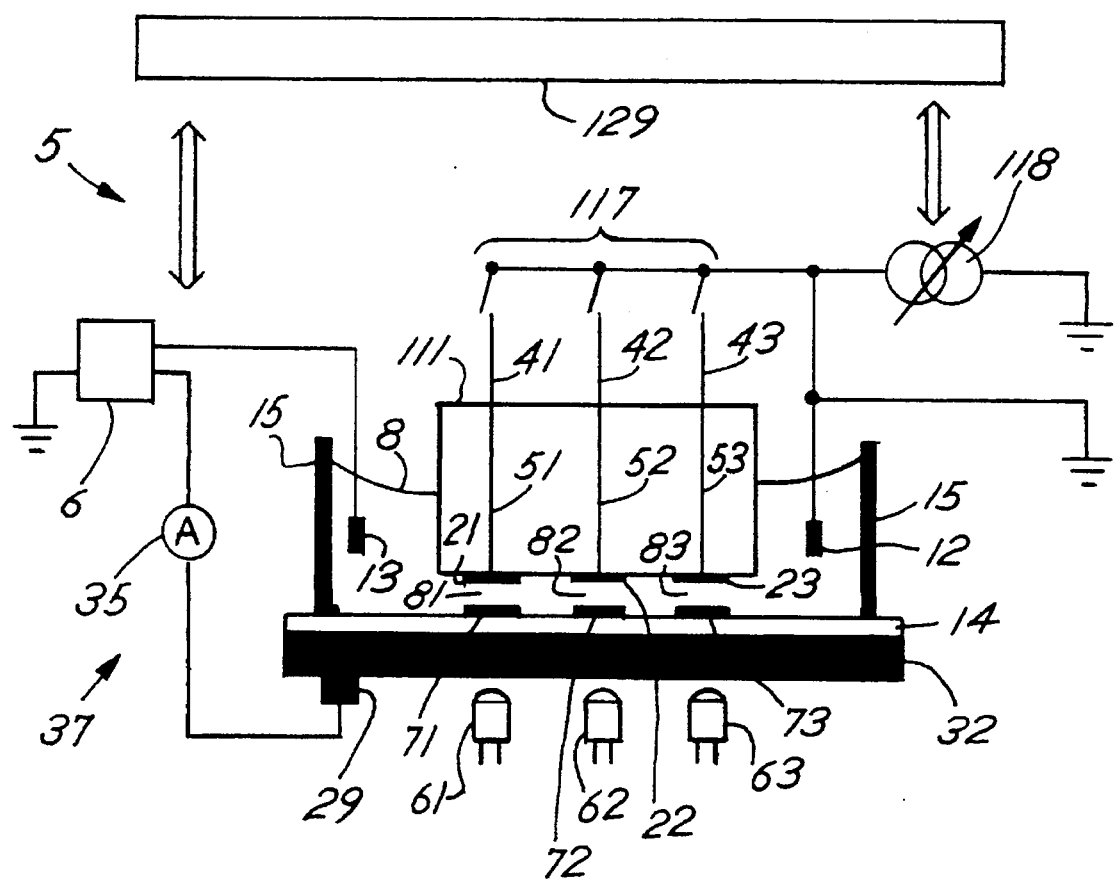
FIG. 1 is a schematic illustration of the preferred embodiment of the electrochemical feedback system of the present invention.

A coulometric feedback system, capable of quantitation at 8 sites, has been developed which comprises of two major parts; a light-addressable potentiometric sensor (LAPS) and a computer-controlled array of feedback electrodes. A coulometric feedback device 5 for carrying-out the present invention is schematically represented, for example, in FIG. 1, and is based on the light-addressable potentiometric sensor (LAPS) device 10 represented for example in FIGS. 2(a), 2(b) and 3.

The LAPS monitors the redox potential of each of the 8 sites and the feedback electrode array 21–28 is used to inject the charge required to stabilize the redox potential at each of the 8 sites. Enzymes capable of altering redox potential are quantitated at each site by measuring the quantity of charge injected during a predetermined time period. This quantity of charge is directly related to the enzyme activity present at each site. This enzyme detection system has greater sensitivity and dynamic range than commercially-available rapid assay systems.

We found that the performance and overall sensitivity of the coulometric feedback system 5 was enhanced 10-fold by utilization of MOS (metal-oxide-silicon) fabrication technology for construction of the feedback electrode array 21–28. With this technology the feedback electrode array 21–28 is constructed in an insulated semiconductor chip 30, as shown for example in FIG. 25, which in the coulometric feedback system 5, directly opposes the LAPS semiconductor chip 32. The feedback electrode array chip 30 has 8 electrode sites 21–28 which are made by sputter-depositing a noble metal in high vacuum. A critical feature in the electrode construction is the fact that electrode leads directly to the backside of the electrode array chip 30 without exposing any bi-metallic junctions 51–58 to the electrolyte 8. Front-to-back noble metal contact is made by micro-machining (i.e. by anisotropically-etching) pyramidal holes 34, as shown for example in FIGS. 7(a)–(d), in both the backside and the front side of the feedback electrode array chip 30 so that the tip of each pyramid meets within the chip 30. The micro-machining step was carried out by the Silicon Processing Group within Molecular Devices. Thus both the feedback electrode array 21–28 and the LAPS semiconductor chip 32 now utilize planar semiconductor fabrication techniques. The fabricated electrode array 21–28 eliminates micro-corrosion of the feedback electrode 21–28, and provides for a stable redox potential at all 8 detection sites. This construction has proven to be reproducible and robust and eliminates the short-circuit micro-currents experienced with the earlier fabrication techniques.

The coulometric feedback system 5 has been validated for 8-site detection of biotinylated β-D-galactosidase bound to commercially-available Threshold® capture membranes 36. Results show that an exponential control algorithm may be used to supply the feedback current while maintaining the redox potential at a steady-state over a wide range of quantitated enzyme activites. Analytical results are obtained easily and quickly over a wide dynamic range of from 1 to $10^5$ picograms of β-D-galactosidase enzyme over at least 3 logs of response signal. Experiments designed to examine "cross-talk" between adjacent analysis sites have indicated no interference.

In the coulometric feedback system 5, redox-potentials are monitored with a redox LAPS chip 32 at multiple-sites on an immunocapture membrane 36. Software, written in C language, provides for control of a feedback current injected into each detection site of the multiple-site feedback electrode array 21–28. The feedback charge during the predetermined time periods are recorded into Excel-formatted files. The total feedback charge required to maintain a constant steady-state redox potential is plotted versus the enzyme concentrations by the Software.

Four redox coupling systems for quantitation of four immunoassay label enzymes have been developed. The enzymes are alkaline phosphatase, horseradish peroxidase, β-D-galactosidase and glucose oxidase. For each of these enzymes we have developed systems employing a substrate, having rapid enzymatic turnover and generating a redox-active product, and a redox oxidized/reduced pair (mediator) which couples both to the product of the enzymatic reaction and to the sensing surface of the LAPS detector 32. Together, these are the four most common immunoassay labeling enzymes employed in both clinical chemistry and analytical chemistry. The enzymes are highly stable and have a high turn-over number.

Light Addressable Potentiometric Sensor (LAPS) Detection Principle

Figure 2A:
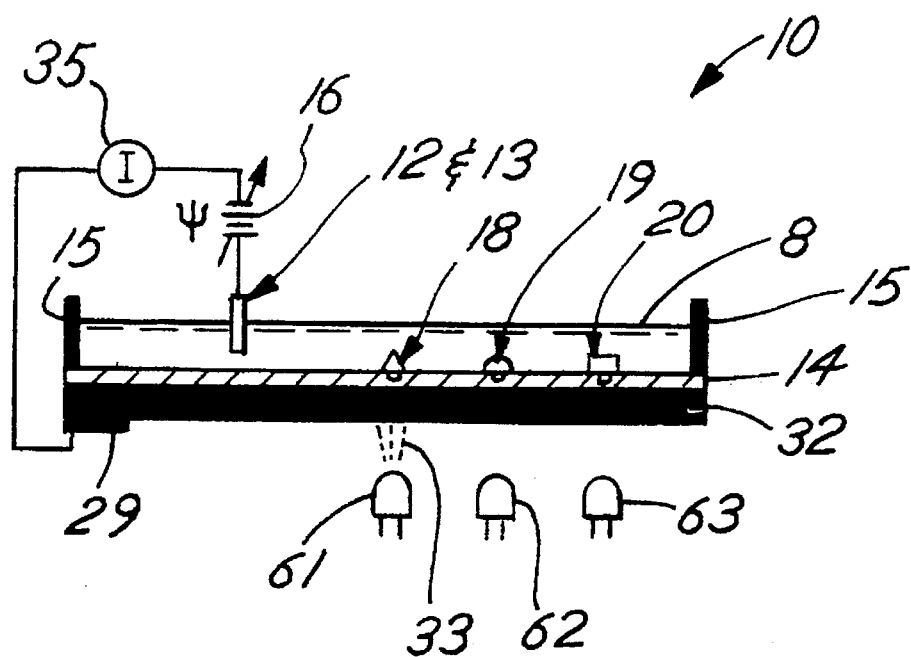
FIG. 2(a) is a schematic illustration of a light-addressable potentiometric sensor (LAPS) device, in which a silicon plate with a surface insulator of silicon nitride in contact with an electrolyte is photo-responsive to four representative light-emitting diodes.
Figure 3:
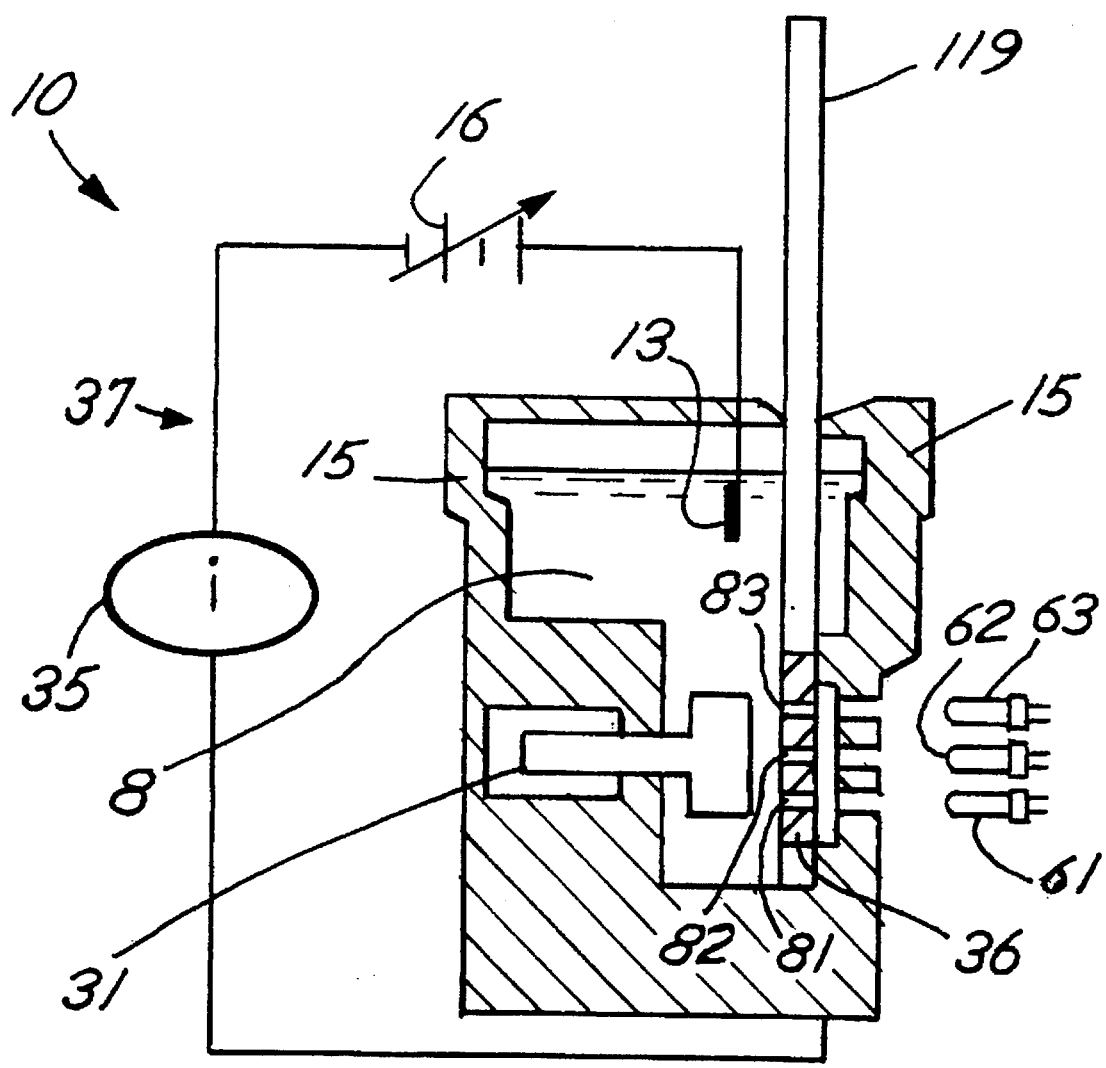
FIG. 3 is an illustration of a light-addressable potentiometric sensor (LAPS) device, showing the Threshold stick, the plunger, and three representative light-emitting diodes.

The essential elements of a LAPS device 10 are shown in FIGS. 2(a) and (b) and 3. The LAPS device 10 includes a thin flat semiconductor plate or silicon chip 32 comprising n- or p-type silicon. A surface of the semiconductor plate 32 is coated with a dielectric 14. The dielectric 14 insulates the semiconductor plate 32 from an aqueous electrolyte 8 containing the analyte or analytes 18–20. Electrolyte reservoir walls 15 contain the aqueous electrolyte 8 on the dielectric 14.

Bias potential or potentiostat 16 in an external circuit is applied between the semiconductor plate 32 and a controlling and reference electrode 12–13, which is designed for electrochemical communication with the aqueous electrolyte 8. An ohmic contact 29 may be used to interface with the semiconductor plate 32. The bias potential or potentiostat 16 can be adjusted to modify the magnitude and direction of an electrical field in the space charge region of the semiconductor plate 32, which is adjacent to the interface of the dielectric 14. Electrode 13 can be composed of, for example, Ag/AgCl. Both controlling and reference electrode functions may be combined in a single electrode because the dielectric 14 prevents direct current from passing through electrode 13. Alternatively, a three electrode potentiostat may be used where separate controlling and reference electrodes are placed into the electrolyte 8 and the working electrode lead of the potentiostat is connected to the semiconductor plate 32 via ohmic contact 29.

Transient illumination of the semiconductor plate 32 produces negative and positive charge carriers as electrons and holes, respectively. These photogenerated electrons and holes migrate in opposite directions when they encounter the electrical fields of the space-charge region. This charge separation produces a photopotential that, in turn, causes a transient photocurrent 35 to flow in an external circuit 37.

Accordingly, a locally directed beam of intensity-modulated light may be used to investigate local electrical fields present within the semiconductor 32. The spacial resolution of this technique depends both upon the cross-sectional dimension of the light beam and the diffusion length of the photogenerated electrons and holes in the semiconductor.

The beam of light may be directed through the dielectric 14 into the space charge region of the semiconductor plate 32 adjacent to dielectric 14. Alternatively, as shown in FIGS. 2(*a*), 2(*b*), and 3, the beam of light 33 may be directed into the semiconductor plate 32 from a side of the semiconductor plate 32 opposite the dielectric 14, provided that the semiconductor plate 32 is thin enough. The illumination may be provided by, for example, the light-emitting diodes 61–68, three of which are shown in FIG. 2(*a*) as L.E.P.s 61–63. Illumination may also be provided by a fiber optic device 17, shown for example in FIG. 2(*b*) (shown with a standard plunger 31).

Carriers that are photogenerated within the semiconductor plate 32 diffuse to the space charge region of the semiconductor plate 32 near the dielectric 14. The diffusion is dependent upon the minority carrier diffusion length of the particular semiconductor material. The dielectric 14 prevents direct (i.e. faradaic) current from passing across the junction between the semiconductor plate 32 and the aqueous electrolyte 8. Accordingly, the modulation of applied light intensity over time produces an alternating, rather than direct, photocurrent 35.

Detection of pH Change with LAPS

The total electric field at any location within the space charge region of the semiconductor 32 is dependent upon the sum of all fixed and variable potentials present in the complete series circuit. These potentials include the applied potential 16, the reference electrode potential, other contact potentials, other potentials due to fixed charges in the dielectric 14, and, most importantly, any surface potential that develops at the interface of the dielectric 14 and the aqueous electrolyte 8.

Dielectric surfaces having Brønstad acid species, i.e. proton donors, such as silanol groups on silicon oxide or silicon nitride dielectrics, for example, become more negatively charged as the pH of the electrolyte is increased. The surface potential of a dielectric 14 of this type is therefore pH-dependent when exposed to an aqueous electrolyte 8. The pH-dependence of this surface potential causes the graphical relationship between photocurrent 35 and applied potential 16 to shift along the potential axis when the pH of the electrolyte 8 is varied. The shift is roughly 59 mv/pH at room temperature, as is predicted from the Nernst relationship.

Therefore, pH measurements are possible as a result of this pH dependency. The use of locally-directed beams of intensity-modulated light allows pH changes to be monitored at local, spatially separate regions of the dielectric surface.

Detection of Specific Ions with LAPS

Chemically-sensitive structures may be placed on the surface of LAPS devices 10 to monitor analytes other than hydrogen ions. For example, specific-ion-sensing membranes may be deposited to fabricate sensing sites for specific ions, e.g. $K^+$. For example, deposition of a valinomycin-containing polyvinyl-chloride membrane results in a spatially-resolved, $K^+$ ion sensor. Intensity-modulated illumination of a region of semiconductor adjacent to the valinomycin-containing polyvinyl-chloride membranes produces an alternating photocurrent 35 similar to that observed with the pH sensing device. In this case, however, the relationship between the measured alternating photocurrent 35 and the applied potential 16, ψ, responds to changes in activity of $K^+$ ion in the electrolyte 8.

Detection of Redox Potential Changes with LAPS

Figure 4:
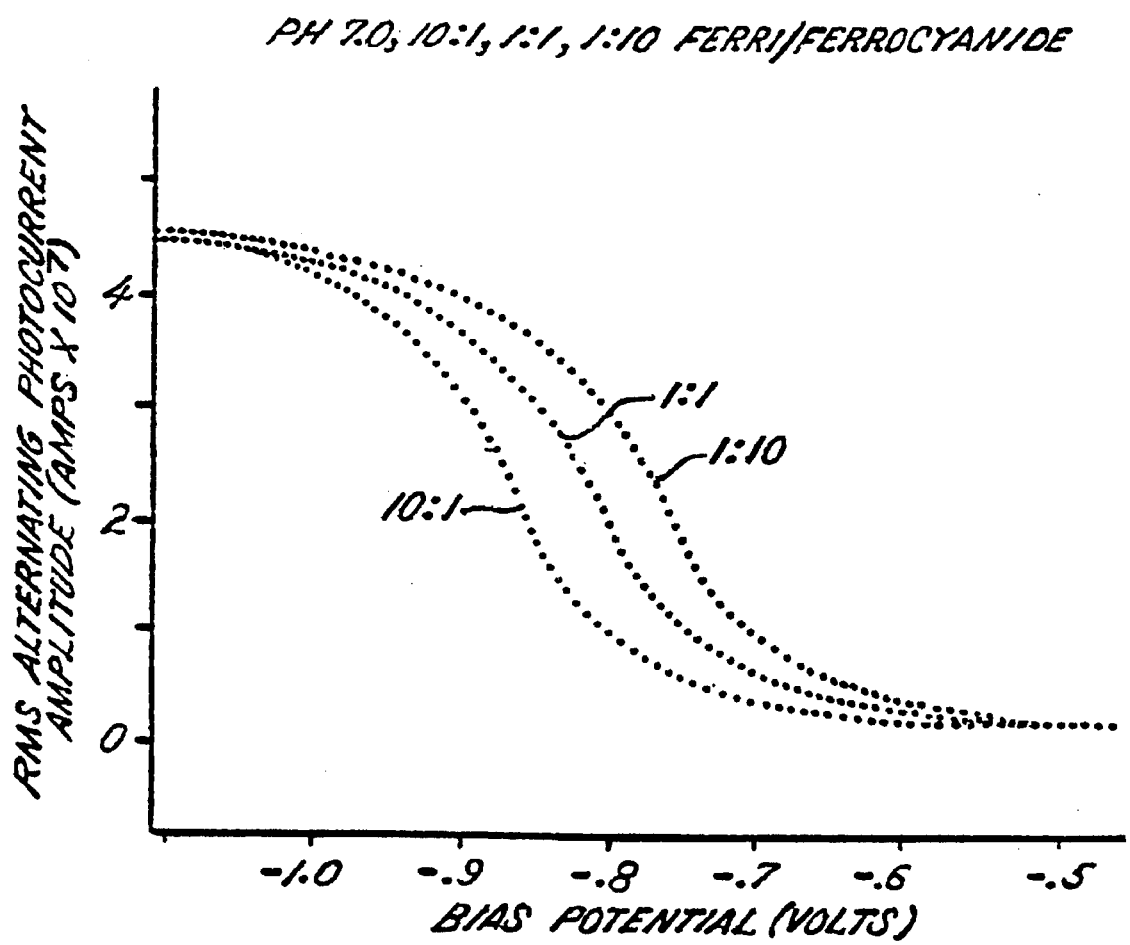
FIG. 4 is a graph which plots alternating photocurrent as a function of bias potential (Volts) for different $Fe(CN)_6^{-3}$/ $Fe(CN)_6^{-4}$ concentration ratios.

Spatially-resolved, redox potential measurements can be made by depositing a thin layer of metallic gold (or other noble metals) 71–78 on the dielectric 14. When the electrolyte solution 8 contains a redox pair, such as ferricyanide-ferrocyanide, the potential of the noble metal 71–78 is determined by the standard redox potential of the redox pair and the ratio of the activities of the members of the redox pair in accordance with the Nernst equation. Intensity-modulated illumination of a region of semiconductor 32 adjacent to the noble metal 71–78 produces an alternating photocurrent 35 similar to that observed with the pH sensing device. In this case, however, the relationship between the measured alternating photocurrent 35 and the applied potential 16, ψ, responds to changes in redox potential of the electrolyte 8. A typical characteristic dependence of the amplitude of the measured alternating current for a LAPS device with gold sensing regions is shown in FIG. 4.

Immunoassay by Quantitation of Rate of pH Change in Micro-Volume Chambers

Specific anti-analyte antibody is used to capture the analyte (18, 19 or 20) onto a immunoassay capture membrane 36. The analyte then is labeled with a second anti-analyte antibody-enzyme conjugate. When the enzyme label catalyzes a reaction that results in a change in redox potential, the amount of enzyme, and therefore also the amount of analyte, is quantitated with a LAPS device 10, modified for redox measurements. Commercially-available Threshold® Immunoassay Systems are based on detection of pH-change. Briefly, an analyte of interest (18, 19, or 20) is captured onto a nitrocellulose membrane 36 by an anti-analyte antibody bound to the membrane 36. (Both the capture antibody and the membrane 36 are biotinylated and are linked to the membrane 36 by tetra-valent streptavidin.) The membrane-bound, analyte molecules are labeled with the enzyme, urease, by employing a second anti-analyte antibody in the form of an antibody-urease conjugate. (The second antibody either is directly conjugated to urease or, alternatively, is derivatized with a fluorescein hapten and bound indirectly to urease via an anti-fluorescein antibody conjugated to urease.)

In the Threshold® Immunoassay System, a LAPS device 10 is used to quantitate the number of urease molecules present at each of 8 detection sites on the capture membrane 36. In the presence of urease, urea is hydrolyzed into 2 molecules of $NH_3$ and 1 molecule of $CO_2$, thereby causing a change in pH. The initial rate of pH change at a detection site is directly proportional to the number or urease molecules at the detection site and is inversely proportional to the buffer capacity present at the site. Because of the low fluid volume, micro-volume detection chambers 81–88 have very low buffer capacity, and thus provide for very high detection sensitivity. For example, Threshold® Immunoassay Systems routinely are used to quantitate microorganisms, human chronic gonadotropin, hybridization of DNA probes, and to monitor the binding agonists and antagonists to the nicotinic acetylcholine receptor. In addition, a kit is available (Molecular Devices Corp.) to quantitate total DNA, with picogram sensitivity.

Comparison of Enzyme Labels Used for pH and Redox Potential Systems

In the commercial Threshold® Immunoassay System, pH-dependent surface potentials are monitored at eight sample Sites. The rate of pH change at each site is directly proportional to the amount of analyte captured and inversely proportional to the pH-buffering capacity present. The 0.63µl liquid reagent present at each site is buffered with 10 mM sodium phosphatase (pH =p$K_a$. =6.8). Decreasing the volumetric buffering capacity further, however, results in only a small increase in rate of pH change due to a high density of pH-buffering species present on the immunoassay capture membrane 36 (both naturally present and nonspecifically adsorbed from analyte samples).

The redox-modified Threshold® Immunoassay System functions similarly to the commercial Threshold® System. The redox-modified system simultaneously monitors rates of change in redox potential (instead of pH) at eight sample sites. Instead of urease enzymes that catalyze changes in redox potential are conjugated to anti-analyte antibodies. The four commonly employed immunoassay enzyme labels, alkaline phosphatase (ALP), horseradish peroxidase (HRP, β-D-galactosidase (β-gal) or glucose oxidase (GO) may be employed to catalyze redox potential changes. For each of these enzymes we have developed a liquid reagent system employing a substrate, having rapid enzymatic turnover, which generates a redoxactive product. The redox reagents systems also employ a redox (oxidized/reduced) pair which couples both to the product of the enzymatic reaction and to the noble metal surface 71–78 of the LAPS detector 10, modified for redox measurement. The redox pair must be stable in the pH range where enzyme activity is optimal and must have the appropriate standard redox potential to be able to accept electrons from the product of the enzymatic reaction. Furthermore, the redox pair must not react with dissolved oxygen and must have an acceptably high electron exchange current density with noble metals to be detected rapidly by LAPS. We have developed such redox systems have for the four enzymes ALP, HRP, β-gal and GO. These enzymes are the four most commonly used ELISA labeling enzymes in both clinical chemistry and analytical chemistry. The components of each system for the four enzymes are discussed below.

Operating Principle of Coulometric Feedback System

The preferred coulometric feedback system 5 consists of a LAPS device 10, modified for redox measurement, with an additional feedback electrode array 21–28. The LAPS 32 is placed in contact with one side of the thin capture membrane 36 and the feedback electrode array 21–28 is placed in contact with the opposite side of the membrane 362 array. The LAPS device monitors the redox potential of each site and the feedback electrode array 21–28 injects the appropriate charge necessary to maintain a constant redox potential. Enzymes such as β-D-galactosidase, horseradish peroxidase, alkaline phosphatase, or glucose oxidase, are quantitated by recording the amount of charge injected over a predetermined injection period. The amount of charge injected is proportional to enzyme activity.

Advantages of Coulometric Feedback System

The redox LAPS coulometric feedback system 5 has several advantages over the commercially-available pH detection LAPS system. First, detection of redox potential changes is about 100 -fold more sensitive than detection of pH changes due to the fact that the capture membrane has a much lower redox buffering capacity than pH buffering capacity. Secondly, due to the fact that precise control of the microvolume is not required with the coulometric feedback system 5, the coulometric feedback system 5 has greater analytical precision. Finally, the dynamic range for quantitation of such rapid enzyme-linked immunoassays is increased in the coulometric feedback system 5 because the feedback electrode array 21–28 is able to counteract the change in chemical potential caused by high concentrations of enzyme in the micro-volume 81–88.

Limit of Enzyme Molecule Detection by Monitoring pH Change in Micro-Volume Chambers The LAPS device 10 in the Threshold® System simultaneously monitors the rate of pH change at eight spatially-separate microvolume sample sites 81–88 on a Threshold capture membrane 36. The relation between the mass of enzyme present at a sample site and the rate of change in the surface potential of the LAPS device is given by:

$$d\psi/dt \propto dpH/dt \qquad [1]$$

where, $$\alpha = d\psi/dpH = 2.303(RT/F) = 59 \ mV \ at \ 25° \ C. \qquad [2]$$

$$dpH/dt = \frac{EA}{V \beta_V^{H^+} + S \beta_S^{H^+}} \qquad [3]$$

$$\beta_V^{H^+} = \text{Volumetric pH Buffer Capacity} = \frac{2.303 * C_{H^+}}{10^y + 2 + 10^{-y}} \qquad [4]$$

$$\beta_S^{H^+} = \text{Surface pH Buffer Capacity} = \frac{2.303 * D_{H^+}}{10^y + 2 + 10^{-y}} \qquad [5]$$

and $$y = pH - pK_a. \qquad [6]$$

in which $d\psi/dt$ is the rate of surface potential change measured at an individual site, R is the gas law constant, T is the absolute temperature, F is the Faraday Constant of 96,500 coulombs/mole, A is the enzyme specific activity, E is the mass of enzyme present, $\beta^H_v$ is the volumetric pH buffer capacity, V is the volume at an individual site, $C_{H^+}$ is the concentration of the pH-buffering species present in solution, $\beta^H_s$ is the surface pH buffer capacity, S is the surface area present at an individual site, $D_H$ is the density of the pH-buffering species on the surfaces present at an individual site. In general $y=pH-pK_a$, which for volumetric buffering capacity is the difference between the pH of the solution and the p$K_a$ of the pH-buffering species present in solution. For the surface buffering capacity pH–p$K_a$ is the difference between the pH at the surface and the $pK_a$ of the surface-bound pH-buffering species. The surface pH may be different than the bulk pH depending on surface charge.

For a given lower instrumental limit in detection of $d\psi/dt$, the sensitivity of the system for detection of enzyme activity, EA, is determined by the volumetric pH buffer capacity and the surface buffer capacity. The volumetric buffer capacity may be minimized by decreasing both the volume and the concentration of pH-buffering species. For example, with 10 mM concentration of pH-buffering species, where $pH=pK_a$, and with a Threshold System microchamber assay volume of 0.64 μl, the volumetric buffer capacity, $V\beta^H_v$, is 6.4 nanomoles. That is, it takes 6.4 nanomoles of $H^+$ ions to change the pH by one unit. The surface buffer capacity, $S\beta^H_s$, is dominated by the high surface area of the nitrocellulose capture membrane and, in contrast to volumetric buffering capacity, is relatively fixed. The measured surface buffer capacity of the nitrocellulose capture membrane, is equivalent to 2.3 mM in the same 0.64μl volume of an individual site, i.e. $S\beta^H_s$ is equal to 1.5 nanomoles. Impurities retained on the membrane 36 from proteinaceous materials adsorbed onto the membrane 36 tend to further increase the buffer capacity. Therefore, it is difficult to reliably improve sensitivity by further reducing the surface buffer capacity.

Limit of Enzyme Molecule Detection by Monitoring Redox Potential Change in Micro-Volume Chambers As mentioned previously, the LAPS detector 10, with noble metal sensing regions 21–28, may be used to monitor redox potential. With this modification, enzymes that catalyze a change in redox potential, rather than a change in pH, may be quantitated with the LAPS in a micro-volume chamber 81–88. Similar to the pH detection case described above, the detection limit for quantitation of such redox enzymes depends on the volumetric and surface redox-buffering capacities of an individual site within the micro-volume detection chamber. Analogous to the pH case, the relation between the mass of the enzyme present in the chamber and the rate of the redox potential change is given by:

$$d\psi/dt = \alpha/n \, d \log (Ox/Red)/dt \quad [7]$$

$$d \log(Ox/Red)/dt = \frac{EA}{V\beta_V^R + S\beta_S^R} \quad [8]$$

$$\beta_V^R = \text{Volumetric Redox-Buffer Capacity} = \frac{2.303 * C_R}{10^w + 2 + 10^{-w}} \quad [9]$$

$$\beta_S^R = \text{Surface Redox-Buffer Capacity} = \frac{2.303 * D_R}{10^w + 2 + 10^{-w}} \quad [10]$$

$$w = \log (Ox/Red) \quad [11]$$

where $\alpha$ is the same as previously given in Eq.[2], Ox/Red is the ratio of the activities of the oxidized and the reduced redox species present, n is the number of electrons transferred to convert the oxidized to the reduced species, $\beta_v^R$ is the volumetric redox-buffering capacity, $\beta_s^R$ is the surface redox-buffering capacity (analogous to the respective volumetric and surface pH-buffering capacities in the pH case), $C_R$ is the concentration of redox-buffering species in the bulk electrolyte 8 and $D_R$ is the density of redox-buffering species on the surfaces at the measurement site. All other terms are the same as defined for the pH case given above.

Because the density of redox active species bound to immunoassay capture membranes 36 is characteristically <1% of pH buffering species, the detection limit for enzyme activity, EA, causing a given change in $d\psi/dt$, characteristically is at least 100-fold better for redox systems compared to pH- systems.

Reagents Sources ImmunoPure biotinylated β-D-galactosidase, biotinylated b-D-glucose oxidase, biotinylated horseradish peroxidase (b-HRP), streptavidin alkaline phosphatase (sa-ALP), 4-(N-maleimidomenthyl)cyclohexane-1-carboxylate (SMCC) were purchased from Pierce (Rockford, Ill.). Bovine serum albumin (BSA), bovine g-globulin (BGG), 3,5,3',5'-tetramethylbenzidene (TMB), 5-bromo-4-chloroindoyl-phosphate disodium salt (BCIP), Phenanzine methosulfate (PMS), p-nitrophenyl-phosphate (p-NPP), bromocresol purple (BCP), 2,2'-azino-bis(3-ethyl-benzthiazoline-6sulfonic acid) (ABTS), tris(hydroxy-methyl)aminomethane and Tween-20 were from Sigma (St. Louis, MO.). 3[1-[(phenylamino)-carbonyl]-3,4-tetrazolium]-bis(4-methoxy -6-nitro)benzene-sulfonic acid hydrate (XTT) was purchased from Polyscience Inc.(Warrington, PA). 5-bromo-4-chloro-3indolyl-β-D-galactopyranoside (X-Gal) was purchased from Gold Biotechnology (St. Louis, MO.). Streptavidin was from SCRIPPS (San Diego, CA.). Anti-fluorescein antibody was purchased from Berkeley Antibody Corp. (BAbCo). Nitrocellulose immuno-capture membranes 36 coated with biotinylated BSA were obtained from Molecular Devices Corp. (Cat. No. R8007, Sunnyvale, CA.).

XTT Redox Mediator

The commercially available oxidized form of XTT was reduced by freshly prepared zinc amalgam, Zn(Hg), in phosphate buffer solution (pH 6.8, 100 mM NaCl). Complete reduction of oxidized XTT by Zn(Hg) is achieved in 45 minutes. Reduced XTT, stored in the dark at 4° C., is stable for at least 1 month. We determined the extinction coefficient for reduced XTT to be 11,000 $cm^{-1}$. Subsequent determinations of the concentration of XTT were carried out by measuring absorbance at 470 nm.

Streptavidin Conjugated ALP (sa-ALP) One mg/ml concentration of sa-ALP was diluted to 1 ng/ml ($1:10^6$ dilution) in Tris buffer (200 mM NaCl, 0.05% Tween-20, 0.1% BGG in 200 mM Trizbase, adjusted to pH 10 with $NaHCO_3$). Excess streptavidin was added at room temperature to give a final streptavidin concentration of 1μg/ml.

Biotinylated Peroxidase (b-HRP) Bound to Streptavidin

One mg/ml of b-HRP was diluted to 1 ng/ml (1:106 dilution) in acetate buffer (200 mM NaCl, 0.05% Tween-20, 0.1% BGG in 200 mM sodium acetate, adjusted to pH 5.5 with HCl). Excess streptavidin was added at room temperature to give a final streptavidin concentration of 1μg/ml.

Biotinylated b-D-Galactosidase (b-gal Bound to Streptavidin

One mg/ml of b-gal was diluted to 1 ng/ml ($1:10^6$ dilution) in wash buffer (Molecular Devices Inc., Sunnyvale, C.A.). Excess streptavidin was added at room temperature to give a final streptavidin concentration of 1 μg/ml.

Biotinylated Glucose Oxidase (b-GO) Bound to Streptavidin

Five mg/ml of b-GO was diluted to 5 ng/ml ($1:10^6$ dilution) in the wash buffer (Molecular Devices Inc., Sunnyvale, C.A.). Excess streptavidin was added at room temperature to give a final streptavidin concentration of 1 μg/ml.

Enzyme Conjugated to Anti-Fluorescein Antibody

Anti-fluorescein antibody conjugated to horseradish peroxidase was purchased from Amersham International (Amersham, UK). Anti-fluorescein antibody conjugated to alkaline phosphatase and anti-fluorescein antibody conjugated to β-D-galactosidase were obtained from Molecular Devices Corporation (Sunnyvale, C.A.).

Alkaline Phosphatase (ALP) Detection

Figure 5:
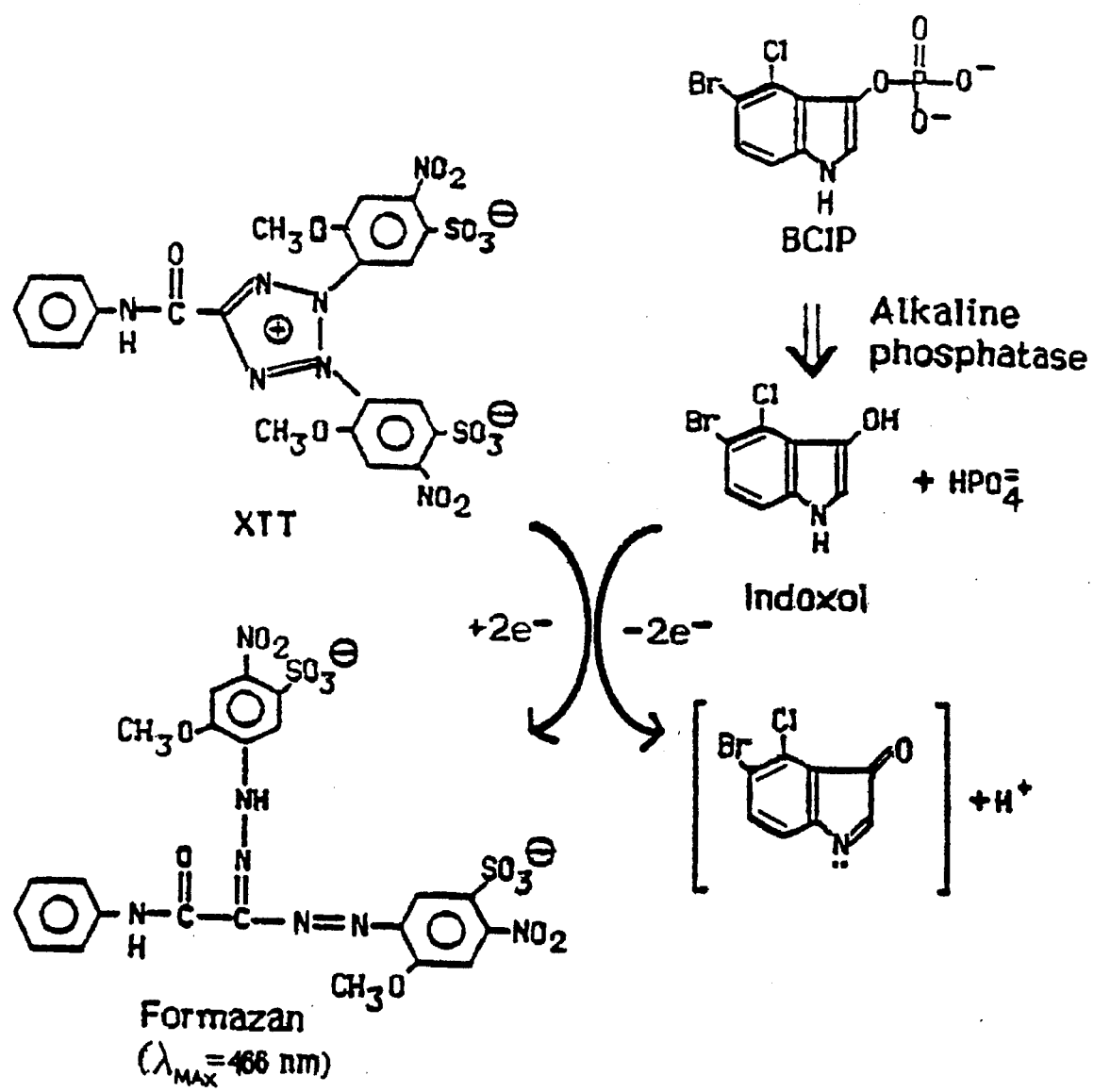
FIG. 5 is a schematic diagram for the alkaline phosphatase redox coupling chemistry.

The redox coupling chemistry employed with LAPS detection of ALP is shown in FIG. 5. Hydrolysis of 5-bromo- 4-chloroindoly-phosphate (BCIP) is catalyzed by ALP to give inorganic phosphate and the bromo-chloro-indolyl (indoxol). Indoxol then reduces a soluble tetrazolium salt (XTT) redox mediator to a corresponding soluble formazan. As the XTT is reduced to the formazan, the redox potential of XTT/formazan pair decreases. The initial rate of change in redox potential is directly proportional to the amount of ALP present.

The alkaline phosphatase-catalyzed reaction is optimal near pH 10. Special care should be taken to ensure that he pH of the redox substrate solution is well-buffered because the redox potential of XTT varies with pH. All of the components including the enzyme substrate, BCIP, are soluble and stable in tris(hydroxymethyl)aminomethane buffer between pH 8 and 10. Furthermore, both the oxidized and reduced forms of XTT are stable at 4° C. at either pH 7.0 or pH 10 for at least two months. This response was measured at room temperature near 25° C. Increasing the temperature to 37° C. likely would produce a further 2-fold further increase in response.

Horseradish Peroxidase (HRP) Detection

Figure 6:
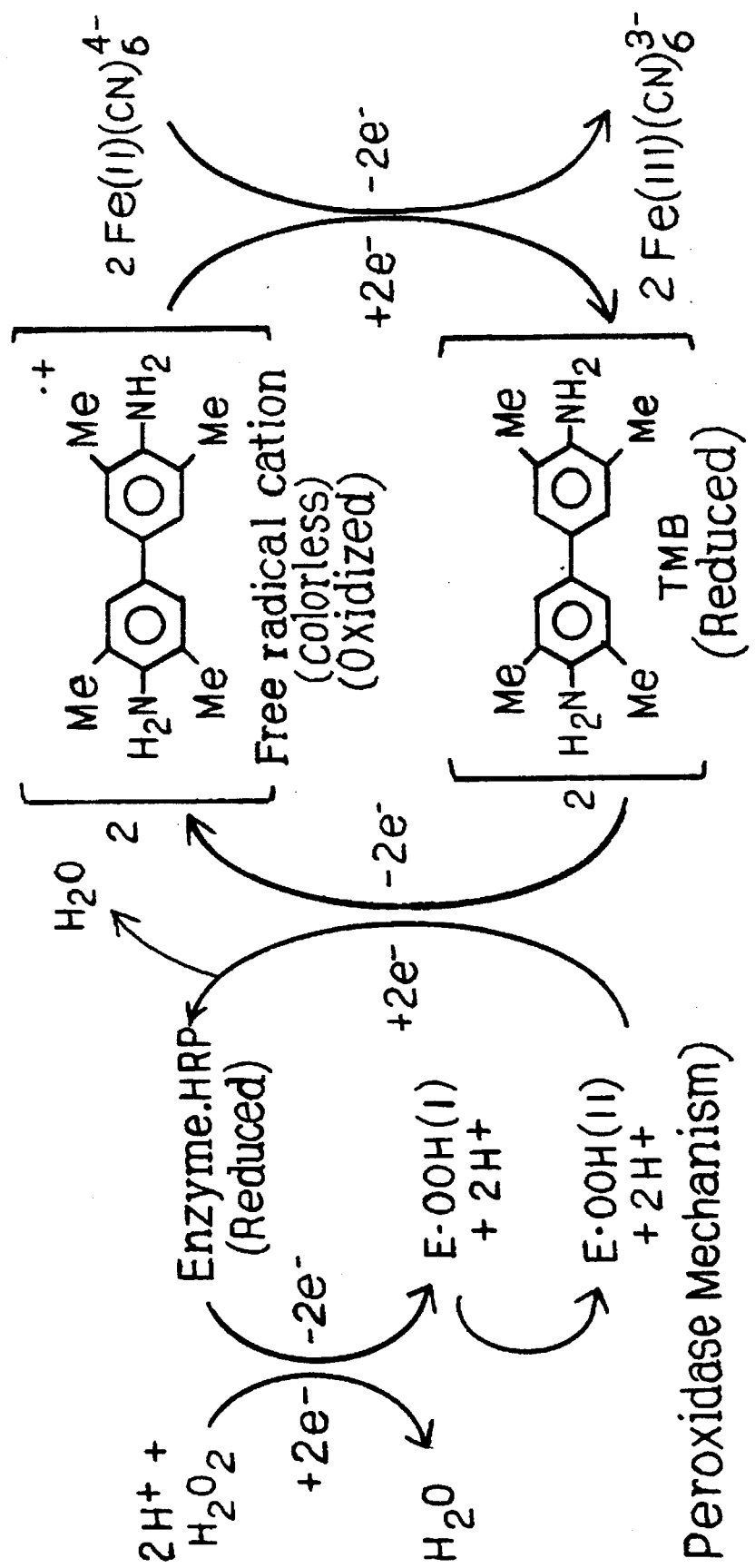
FIG. 6 is a schematic diagram for the horseradish peroxidase redox coupling chemistry.
Figure 7A:
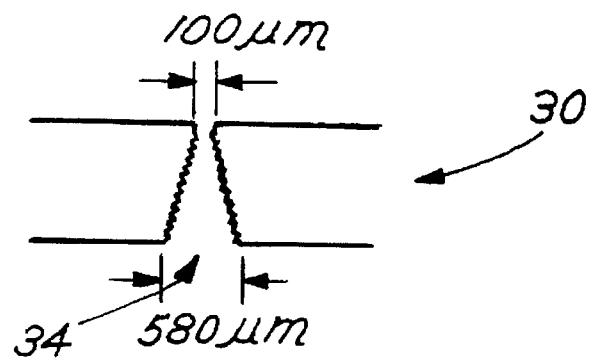
FIG. 7(a) shows steps one and two of the process for fabrication of the feedback electrode array, which involve depositing and patterning photoresist and anisotropically etch through-vias in silicon.
Figure 7B:
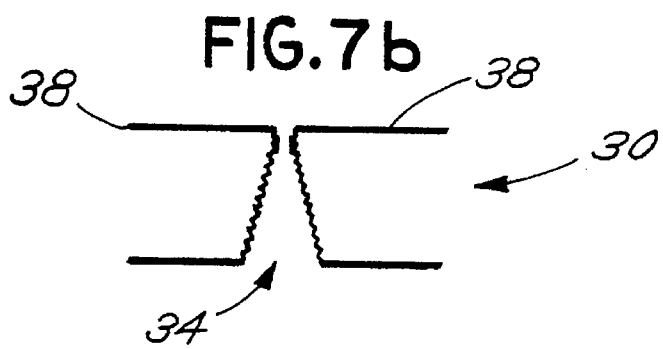
FIG. 7(b) shows step three of the process for fabrication of the feedback electrode array, which involves growing (10 kilo-angstroms silicon oxide.
Figure 7C:
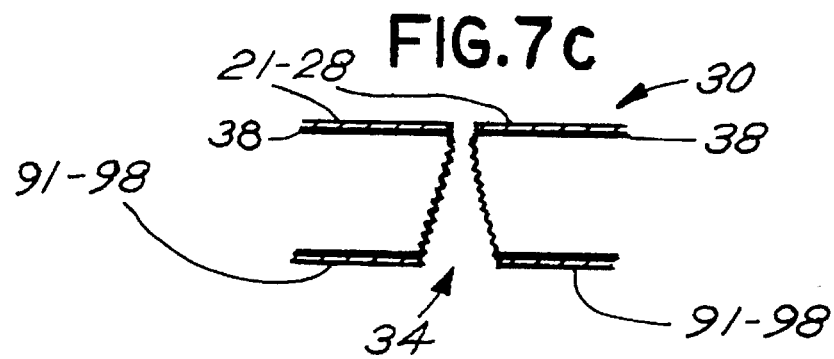
FIG. 7(c) shows step four of the process for fabrication of the feedback electrode array, which involves sputter depositing 10 kilo-angstroms gold in through-vias for electrodes and back side contacts.
Figure 7D:
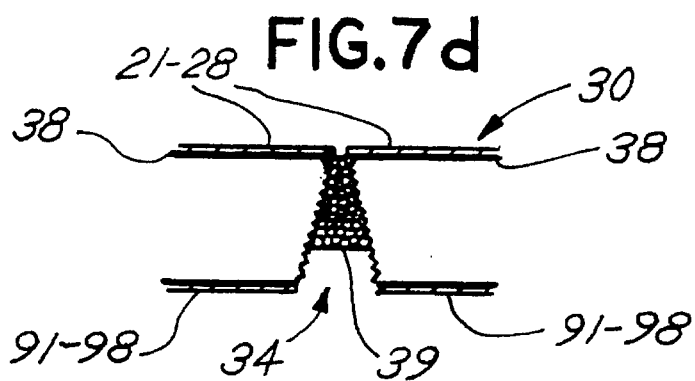
FIG. 7(d) shows step five of the process for fabrication of the feedback electrode array, which involves sealing through-vias with silicone rubber.

The enzyme substrate and redox coupling chemistry that we employ with LAPS is shown in FIG. 6. The enzyme is oxidized by hydrogen peroxide giving an oxidized intermediate (compound I). Compound I is reduced by the hydrogen donors, 3,5,3',5'-tetramethylbenzidene (TMB), in two, one-electron, steps (first to compound II and then back to the native enzyme form). In the process, two molecules of TMB$^+$radical are formed. We employ ferrocyanide to reduce the TMB$^+$-radical back to TMB, oxidizing ferrocyanide (Fe II) to ferricyanide (Fe III) in the process. The ferrocyanide/ferricyanide redox couple may be employed because the pH optimum for HRP is near pH 7 where this redox couple is stable. The TMB substrate dissolves in 1:1 water/ethanol but not readily in pure water. Because TMB is sensitive to light, care should be taken to store it in a dark bottle. The enzyme-catalyzed reaction consumes hydrogen peroxide and ferrocyanide but regenerates the TMB enzyme substrate. The ratio of Fe(II)/Fe(III) decreases when HRP is present together with hydrogen peroxide and TMB. Consequently, the redox potential measured at the LAPS electrode increases. Also, in the presence of peroxides, HRP is short-lived. Hence the sensitivity of detection HRP is best in short assays at temperatures less than 25 ° C. Even with these limitations, however, HRP may also be used as a sensitive immunoassay label.

β-D-Galactosidase (β-gal Redox-Coupling Chemistry

The enzyme substrate and redox coupling chemistry that we employ with LAPS detection of β-gal is similar to the system used for ALP. Because the pH optimum for β-gal is near pH 7, however, the ferrocyanide/ferricyanide redox couple is employed instead of the XTT/formazan redox couple. Shown below reaction [12] catalyzed by β-D-galactosidase is the hydrolysis of 5-bromo-4-chloro- 3-indolyl-β-D-galactopyranoside (X-Gal) to give inorganic galactoside and bromo-chloro-indolyl (indoxol). In reaction [13] the indoxol subsequently reduces ferricyanide to ferrocyanide. The redox potential of ferri/ferrocyanide pair therefore decreases as the reaction proceeds.

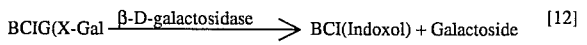

$$BCI\ (Indoxol) + Fe(CN)_6^{3-} \rightarrow [BCI]^+ + Fe(CN)_6^{4-} \quad [13]$$

Similar to the reactions catalyzed by ALP and HRP, the initial rate of change in redox potential is directly proportional to the amount of β-gal present on the immuno-capture membrane 36 and is inversely proportional to both the volume and the volumetric redox buffer capacity. The X-gal substrate is quite stable in PBS solution near pH 7.0.

Glucose Oxidase (GO) Redox-Coupling Chemistry

The enzyme substrate and redox coupling chemistry that we employ with LAPS detection of glucose oxidase is shown in reactions [15]–[17] below. Because the pH optimum for glucose oxidase is near pH 7, the ferrocyanide/ferricyanide redox couple may be employed. The reaction of ferricyanide with GO(FAD)H$_2$, however, is slow and therefore requires the use of a secondary mediator, e.g. phenazine methosulfate (PMS) as acatalyst. The secondary mediator, PMS, is light sensitive and is prepared fresh on a daily basis. In reaction [15] glucose reduces the oxidized form of glucose oxidase, GO(FAD), to the corresponding reduced form, GO(FAD)H$_2$. In reaction [16] GO(FAD)H$_2$ reduces two molecules of PMS to two molecules of PMSH. In reaction [17] PMSH is oxidized by ferricyanide to form ferrocyanide. The redox potential of the ferri/ferrocyanide couple therefore decreases as the reaction proceeds.

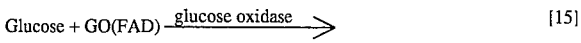

Gluconolactone + GO(FAD)H$_2$ $$GO(FAD)H_2 + 2\ PMS \rightarrow GO(FAD) + 2\ PMSH \quad [16]$$

$$2\ PMSH + 2\ Fe(CN)_6^{3-} \rightarrow 2\ PMS + 2\ Fe(CN)_6^{4-} + 2\ H^+ \quad [17]$$

Similar to the reactions catalyzed by ALP, HRP and β-gal, the initial rate of change in redox potential is directly proportional to the amount of glucose oxidase present and is inversely proportional to both the volume and the volumetric redox buffer capacity ($\Theta^R_v$), as described by Eq. 8.

Enzyme Substrate Reagents

The HRP substrate reagent was composed of 400μM of TMB and 670μM H$_2$O$_2$ in HRP redox buffer which was composed of 100 μM K$_3$Fe(CN)$_6$, 100 μM K$_4$Fe(CN)$_6$, 200 mM NaCl, 0.05% Tween-20 and 0.1% BGG in 200 mM sodium acetate buffer, pH 5.5 (adjusted with HCl).

The ALP substrate reagent was composed of 5 mM BCIP in ALP redox buffer which was composed of 50μM reduced XTT, 50μM oxidized XTT, 1M MgCl$_2$, 10μM ZnCl$_2$, 200 mM NaCl, 0.05% Tween-20 and 0.1% BGG in 200 mM Tris buffer, pH 10 (adjusted with NaHCO$_3$).

The β-gal substrate reagent was composed of 5 mM X-Gal in β-gal redox buffer. For potentiometric determinations, the redox buffer was composed of 100μM K$_3$Fe(CN)$_6$ and 100μM K$_4$Fe(CN)$_6$ in wash buffer (Molecular Devices Inc., Sunnyvale, C.A.). For coulometric feedback determinations, the redox buffer was composed of 1.00 mM K$_3$Fe(CN)$_6$ and 10μM K$_4$Fe(CN)$_6$ in wash buffer. This buffer is denoted as coulometric feedback β-gal redox buffer and the substrate reagent with this buffer is denoted as coulometric feedback β-gal substrate reagent. The GO substrate reagent was composed of 41.6 mM glucose in GO redox buffer which was composed of 362 μM PMS, 100 μM of K$_3$Fe(CN)$_6$ and 100 μM K$_4$Fe(CN)$_6$ in wash buffer. All enzyme substrate reagents were filtered through a 2 μm sterile filter prior to use.

Membrane-Bound Redox Enzyme Activity Determined Potentiometrically (without Coulometric Feedback)

Prior to each determination of enzyme activity, 0.5 ml of the appropriate redox buffer for the enzyme was washed through the nitrocellulose immuno-capture membrane at 500 μl/min flow rate. Next, 200 μl of test sample solutions were filtered through the membranes at a rate of 100 μl/min.

The test sample solutions were either a) streptavidin-ALP; b) streptavidin-biotinylated HRP complex; c) streptavidin-biotinylated-β-gal complex; or d) streptavidin-biotinylated-GO complex. In each case the enzyme was captured via streptavidin to the biotin-coated membrane 36. Next, the membrane 36 was washed with 0.5 ml of the appropriate redox buffer solution at a rate of 500 μl/min. This washing procedure establishes a reproducible, fixed, buffer capacity in the membrane 36 prior to initiation of the rate measurement. The immuno-capture membranes 36 then were stored in the same buffer until transferred to the micro-volume LAPS detection chamber 81–88 which contained the appropriate enzyme substrate reagent for determination of enzyme activity. The reactions catalyzed by alkaline phosphatase, glucose oxidase or β-D-galactosidase causes a decrease in redox potential and that catalyzed by horseradish peroxidase causes an increase in redox potential. The signs of the rates reported by the Threshold® System are reversed (because the reference electrode potential required to maintain constant photocurrent is reported) therefore the rates are positive while quantitating alkaline phosphatase, glucose oxidase or β-D-galactosidase and negative while quantitating horseradish peroxidase. In each case, however, the initial slope (measured by the LAPS device 10 in the Threshold System) is proportional to the amount of enzyme present on the immuno-capture membrane 36.

The commercially available Threshold® System utilized for these measurements monitors the rate of change of the surface potential as a function of time for a period of 90 seconds. The rate of change in redox potential then is calculated from a linear fit of the data. Nonlinear rates of surface potential change lead to poor assay precision. Therefore, the ratio of oxidized and reduced redox species concentrations were maintained near 1:1 where the rates of surface potential change were most linear over the 90 second period. Best results were obtained with 100 μM of reduced and 100 μM oxidized XTT for the ALP assay, and 100 μM $K_3Fe(CN)_6$ and 100 μM $K_4Fe(CN)_6$ for the HRP, glucose oxidase, and β-D-galactosidase assays.

Additional non-linearity in rate may be caused by substrate depletion in the presence of high enzyme activity with non-saturating concentrations of enzyme substrate in micro-volume reaction chambers 81–88. This non-linearity may be prevented by increasing the substrate concentration to 5 to 10 times higher than the enzyme-substrate $K_m$ value. In this way the enzymatic rate remains nearly constant during the 90 second rate measurement.

Model Immunoassay for Universal Standard Reagent

Universal Standard Reagent (USR) is BSA labeled with both biotin and fluorescein and is part of an ILA™ kit (Cat. No. R9003 available from Molecular Devices Corp., Sunnyvale, C.A.). In the pH detection mode we employed the anti-fluorescein antibody-urease conjugate provided with the ILA™ -kit. In the redox detection mode we employed anti-fluorescein antibody conjugated to either ALP, HRP or β-gal. In each case, variable amounts of USR, streptavidin (1 μ/test) and anti-fluorescein antibody-enzyme conjugate (100 ng/test) were pipetted into test tubes, mixed and allowed to bind for 5 minutes at room temperature.

Fabrication of the Coulometric Feedback Electrode Array Chip

Double polished silicon wafers 30 were purchased from SEH, (N<100>, 15–30 Ohm) with 10 kilo-angstroms masking oxide. Coulometric feedback electrode array chips 30 were constructed in the following 6 steps, also shown in FIGS. 7(a)–(d):

1. Through-vias were located in silicon wafers at desired feedback electrode sites by applying a photoresist (Shipley SPR2-1.3 positive resist, spun to 1 micron thickness at 500 rps). The photoresist was applied to both sides of the wafers. The photoresist by on the electrode-side of the wafer was illuminated through a photomask to initiate formation of a 40 micron square opening at each electrode site. Similarly, the photoresist on the back-side of the wafer was illuminated through a photomask to initiate formation of 580 micron square openings at the corresponding site. Precise front-to-back alignment of the photomasks was required. Alignment was make with respect to the wafer flat and was performed with a Karl Suss mask aligner.

2. Tetramethyl ammonium hydroxide (TMAH, quaternary ammonia) at 65° C. was used to anisotropically etch the wafers was at a nominal rate 10 microns per hour. The anisotropic etching process self-terminates on <111>planes within the silicon crystal. The electrode side and backside etches were performed simultaneously. Wafers were rotated during the etch procedure to ensure uniformity. The etching process was terminated from 42 to 44 hours after initiation of the etch when visual inspection showed that through-vias were opened all the way through the wafers. The corners of the etch intersection point within the through-vias then was rounded by a brief isotropic etch (10:1 $HNO_3$:HF).

3. A ten (10) kilo-angstrom thickness layer of silicon oxide 38 was grown in dry oxygen in order to insulate the silicon substrate from metal subsequently deposited.

4. Gold electrodes 21–28 were deposited on the electrode-side of the wafers by sputtering (through a shadow mask with 3.00 millimeter diameter holes centered at the through vias). First ~500 angstroms of chromium (as an adhesion layer) was deposited followed by 10 angstroms of gold. Similarly, gold contact pads 91–98 for contact with the pogo pins 101–108 were deposited on the backside of the wafer by sputtering the chromium and gold layers (through similar shadow masks centered at the through vias on the back-side of the wafers). The metal layers also are deposited within the through vias by this process thereby creating electrical continuity through the vias.

5. The metallized through-vias subsequently were sealed against fluid leakage by application of a small amount of RTV Silicone Rubber (Dow Coring 3140) 39 so as to completely fill, but not overfill, the vias.

6. Front-to-back electrical continuity of each electrode site was checked and the wafers were diced to produce feedback electrode chips 30.

Coulometric Feedback Reader Assembly

Figure 8A:
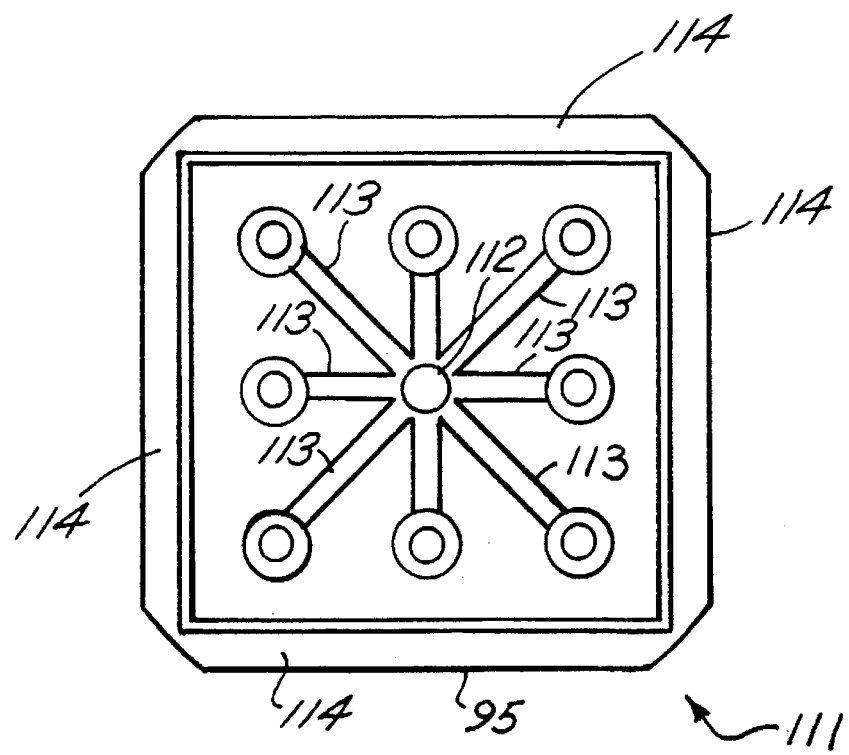
FIG. 8 shows the configuration of a specially fabricated coulometric feedback plunger for the Threshold® Reader Chamber, wherein the feedback electrode chip was installed and sealed into the plunger top with RTV silicon rubber, and the leads for connection to a current source are led from pogo pins (that contact gold contact pads on the back of the chip) through the center of the plunger step and to the back-side of a Threshold® Reader Chamber, whereby contact of the leads with the electrolyte is avoided.
Figure 8B:
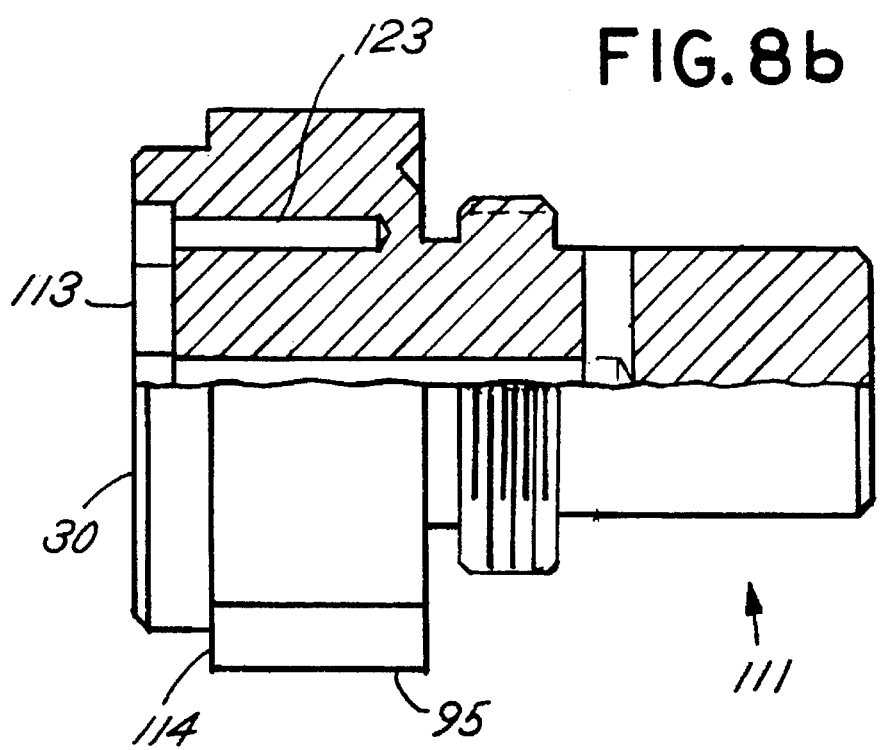
Figure 9:
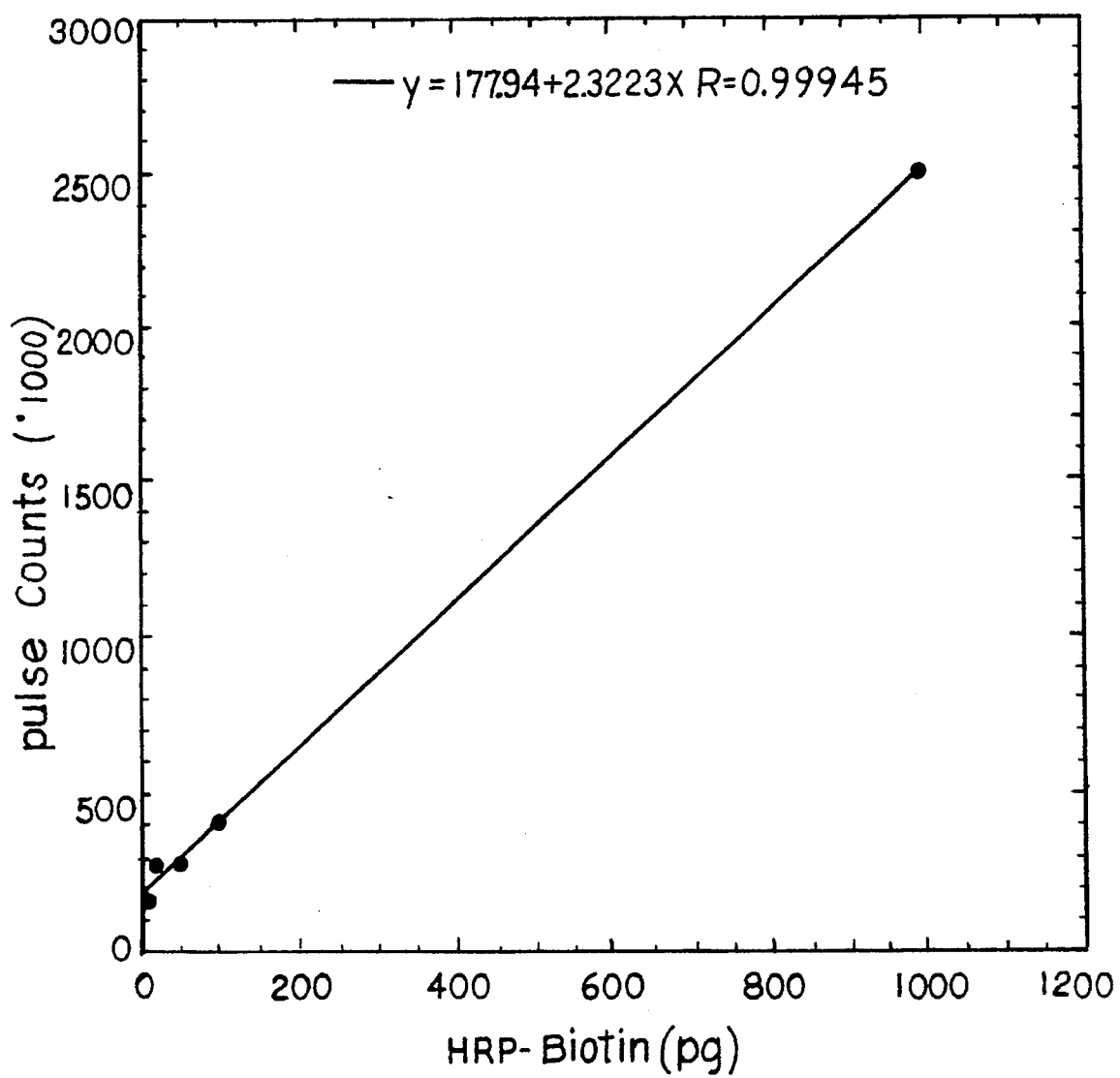
FIG. 9 is a standard curve representing the amount of potentiometric coulometric feedback necessary to maintain a substantially constant redox potential, relative to the amount of enzyme present in the localized electrolyte region.
Figure 25:
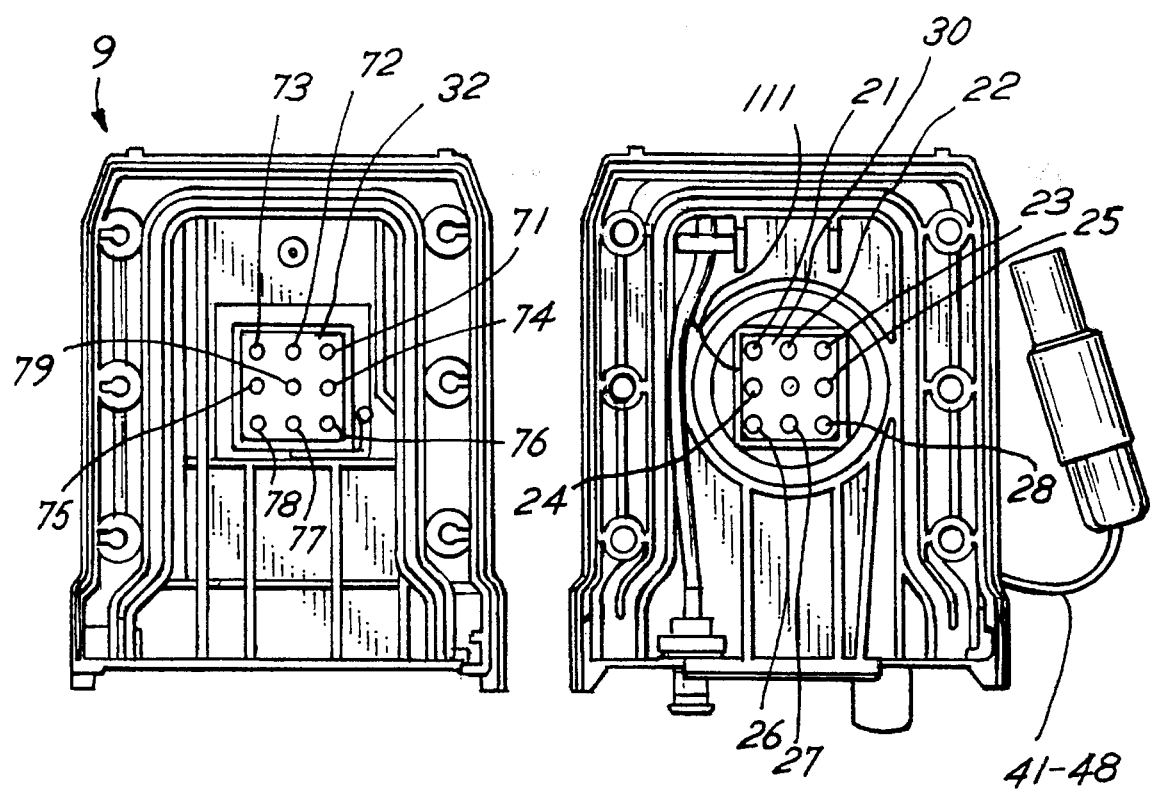
FIG. 25 shows the preferred coulometric feedback reader assembly, opened to show the two halves, wherein the LAPS chip is shown on the left-hand portion, which faces the coulometric feedback array shown on the right-hand portion when the assembly is closed.

On one side of the coulometric feedback reader assembly 9, as shown in FIG. 25, is the redox LAPS chip 32. On the other side of the feedback reader assembly 9 is the current feedback electrode chip 30. The coulometric feedback electrode array chip 30 was installed in a specially-fabricated coulometric feedback plunger 111. The construction of the plunger 111 is shown in FIGS. 8a and 8b. The specially fabricated plunger 111 has a hollow stem 112 and recessed grooves 113 to allow wire leads 41–48 to pass from an outside circuit to each of the electrode contact sites 91–98 on the backside of the feedback electrode chip 30. Pogo pins 101–108, 5/16" in length, soldered to the wire leads 41–48 contact each gold contact pad 91–98 on the back of a coulometric feedback electrode array chip 30 when the chip 30 is inserted into the plunger 111. Pogo pins (not shown) fit in plunger 111 at locations 121–128. RTV (Dow Coming 3140) is applied to fill grooves 113. RTV is also applied to a recessed surface 114 of the plunger 111 around the outer perimeter of the chip 30 to seal the chip 30 to the plunger 111. This construction completely avoids submersion of wire leads 41–48 or bi-metallic junctions 51-58 into electrolytes 8.

Next, a coulometric feedback Reader Assembly 9 was made from the coulometric feedback plunger 111, having the coulometric feedback array chip 30, and a Threshold® reader chamber fitted with a redox LAPS electrode array 32 having 8 redox potential-sensing sites. When assembled, the coulometric feedback Reader Assembly 9 has the 8 electrode sites of coulometric feedback electrode array chip 30 aligned with the 8 redox potential-sensing sites of the redox LAPS electrode 32. The alignment between the sensing and feedback electrodes permits a feedback current to be delivered to each micro-volume chamber 81–88 when the LAPS redox sensing sites detect a redox potential change. In this way a constant redox potential may be maintained at each sensing site.

Figure 2B:
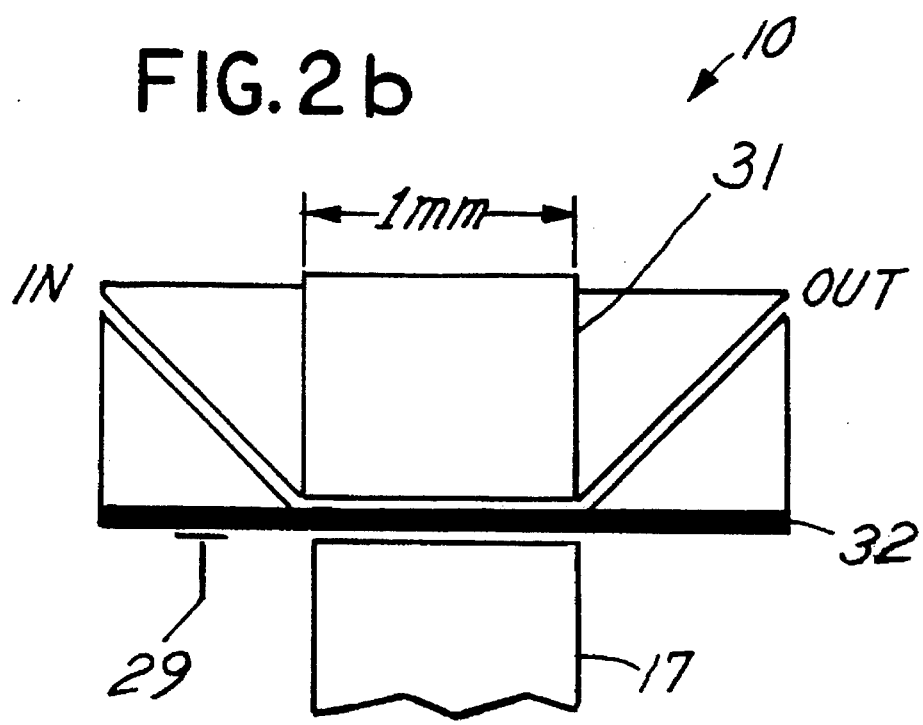
FIG. 2(b) is a schematic illustration of a light-addressable potentiometric sensor (LAPS) device for high-sensitivity measurements of enzyme activity, where it is advantageous to localize the enzyme molecules in a small volume so that they are present at a high effective concentration.

The coulometric feedback system 5 shown in FIG. 1 for carrying out the present invention includes a LAPS device 10 modified for redox mode detection. The redox mode LAPS device is driven by a computer 129 operating with hardware and software designed for driving an applied potential from a potentiostat 6 versus a reference electrode 13, delivering intensity-modulated light to the semiconductor 32 through the light-emitting diodes 61–68, acquiring measurements of the resulting alternating photocurrent 35, and measuring the changes in the relationship between the alternating photocurrent 35 and the applied potential from potentiostat 6 at multiple, independent microvolume sites 81–88.

The computer 129 also provides for coulometric feedback control to the feedback electrodes 21–28 through a computer-controllable, multiple-channel, variable current source 118, such as a Kiethley Model 236 Source Measure Unit or a Kiethley Model 220 programmable current source. The direct current path of the coulometric feedback is completed to ground through a controlling electrode 12, which is situated within the electrolyte reservoir walls 15 and designed for electrochemical communication with the aqueous electrolyte 8.

Electrode switches 117 provide for selection among feedback electrodes 21–28, and may also be computer controlled to automatically select any or all of the monitored microvolume sites 81–88 for coulometric feedback at any given time. If desired, the feedback electrodes 21–28 may be selected such that coulometric feedback may be performed at one or more microvolume sites while basic potentiometric quantitation is conducted at the remaining microvolume sites.

The resulting feedback data may then be used to determine the amount of biochemical agents present. The LAPS data may be digitally filtered to provide the proper time constant for averaging data so as to minimize system noise.

In the Threshold® Immunoassay System employed to obtain the results shown in FIGS. 11–14 without coulometric feedback, it is desirable to minimize the volume of each enzyme detection site on the immunocapture membrane. As shown by Equations [1] through [11], a smaller volume always gives a greater potential change for a given amount of enzyme. In the coulometric feedback device, where the electrolyte is maintained at constant potential, the relationship between enzyme and feedback charge is independent of volume. Minimization of the volume remains advantageous, however, because a change in potential must be detected by the detection electrode before the desired feedback current can be supplied by the feedback electrode. At larger volumes, the measurement system is incapable of detecting small amounts of enzyme when noise in the potential measurement exceeds the amount of potential change caused by the small amount of enzyme present. Thus, reducing the detection volume improves the signal-to-noise ratio for detection of small amounts of enzyme both with and without coulometric feedback. In the coulometric feedback device, however, reducing the detection volume no longer affects the calibration relationship between enzyme and feedback charge. The coulometric feedback method, therefore, is likely to improve the precision with which small amounts enzyme may be quantitated.

One function of moveable plunger 111, shown schematically in FIG. 1, is to minimize electrolyte volume at each detection site on the immunocapture membrane 36. The plunger 111 displaces the buffering electrolyte 8, thereby preventing the transport of buffering species to the detection site either by convection or diffusion. The volumetric buffer capacity of the electrolyte 8 in the region of the enzyme, catalyzing the redox-potential-altering reaction, thereby is minimized. Thus, the signal-to-noise ratio of the enzyme quantitation is improved as electrolyte buffering capacity is displaced when plunger 111 moves from a distal position to a proximal confronting position on the capture membrane 36. Still another function of moveable plunger 111 is to provide one or more independent feedback electrodes 21–28 to the respective one or more independent microvolume sites 81–88.

FIG. 8a and 8b are is a schematic drawings of an eight-site coulometric feedback plunger 111 designed to be used with a Threshold® System. The plunger 31 within a commercial Molecular Devices Corp. Threshold® reader was removed and replaced with the eight-site coulometric feedback electrode plunger 111 having feedback electrode array chip 30. Plunger 111 is made of 30% glass-filled NORYL obtained from General Electric Corporation. Any other suitable rigid insulating polymer, such as Teflon, Delrin, Plexiglas or Kel-F, or nonconductive glass or ceramic may be used.

When, for example, the present Threshold® System is used in combination with a coulometric feedback system as described above, a highly sensitive, precise and reliable system may be realized for rapid detection of biochemical agents that catalyze a redox potential change.

Because the assay volume no longer affects the precision of the results, a smaller electrolyte microvolume can be used in the detection of enzymes. As described above with respect to equation [8], a decrease in the electrolyte microvolume, V, increases proportionally the sensitivity of enzyme detection system. Higher sensitivity is realized when the enzyme molecules are localized in a small volume so that they are present in the system at a high effective concentration.

The dynamic range associated with coulometric feedback is determined by the maximum, diffusion controlled, current density at the controlling electrode at any given concentration of redox mediators present. With respect to the LAPS technology described above, the dynamic range is inversely related to the distance between the feedback electrode array 30 and the LAPS chip 32. With 100 microns of separation between the array 30 and chip 32, a dynamic range of approximately five orders of magnitude can be realized; from about 0.1 picomoles to less than 1 attomole of enzyme). On the other hand, the present Threshold® System, in the pH mode of detection, has a maximal dynamic range of approximately three orders of magnitude; from about 0.1 picomoles to 100 attomoles of enzyme.

While the preferred embodiment discussed above and illustrated in the figures contemplates the use of a semiconductor-based electrode, such as that which is used in the LAPS technology, to monitor the electrolyte redox potential, it will be understood by those skilled in the art that the present invention is not limited to such a configuration. Rather, other types of electrodes, including disposable carbon sheet electrodes, for example, can be used instead to monitor the redox potential of the electrolyte microvolume. Alternatively, platinum, gold, iridium, or other noble metal electrodes may be used to monitor the redox potential. The electrodes may be thin films of noble metal printed onto inert insulating materials. Still another possibility is use of printed carbon electrodes which have been treated with noble metal depositing substances, such as chloroplatinic acid. In this way the electrodes may be made inexpensively but made to measure, reversibly, any change in redox potential.

Still another embodiment (not shown) is where just one electrode per detection site is employed to both measure the redox potential and to provide the feedback current to maintain the redox potential constant. Constant potential amperometry may be employed. In this case, the current required to keep the redox potential constant should be proportional to the amount of enzyme present at an individual site on the immunocapture membrane. A potential problem with constant potential amperometry, however, is that interfering substances, such as proteins present at the electrode-electrolyte interface may impede the flow of faradaic current across this interface. In this case, a substantial faradaic impedance (IR drop) will occur at the electrode-electrolyte interface and the electrolyte will no longer be maintained at constant potential. This problem is prevented in the two-electrode per site systems where the first electrode measures the redox potential and the second electrode provides the feedback current or charge necessary to maintain the redox potential at its desired level. Another way to circumvent this problem with a single electrode, however, is to alternately use the single electrode to measure the redox potential and to provide the desired feedback current. These two functions may be separated in the time domain so that substantially no IR drop appears at the electrode-electrolyte interface during the time interval when redox potential is being measured. In this case the redox electrode could monitor the electrolyte for any change in redox potential. In the event a change is detected, the requisite pulse of current, or charge, could be delivered so as to maintain the redox potential at the desired level. After a suitable period of time following the current or charge pulse, allowing one or more time constants for decay of the polarization potential, the redox potential could again be measured. This procedure would be repeated one or more time in sequence so as to maintain the redox potential of the electrolyte over time precisely at the desired level.

Figure 17:
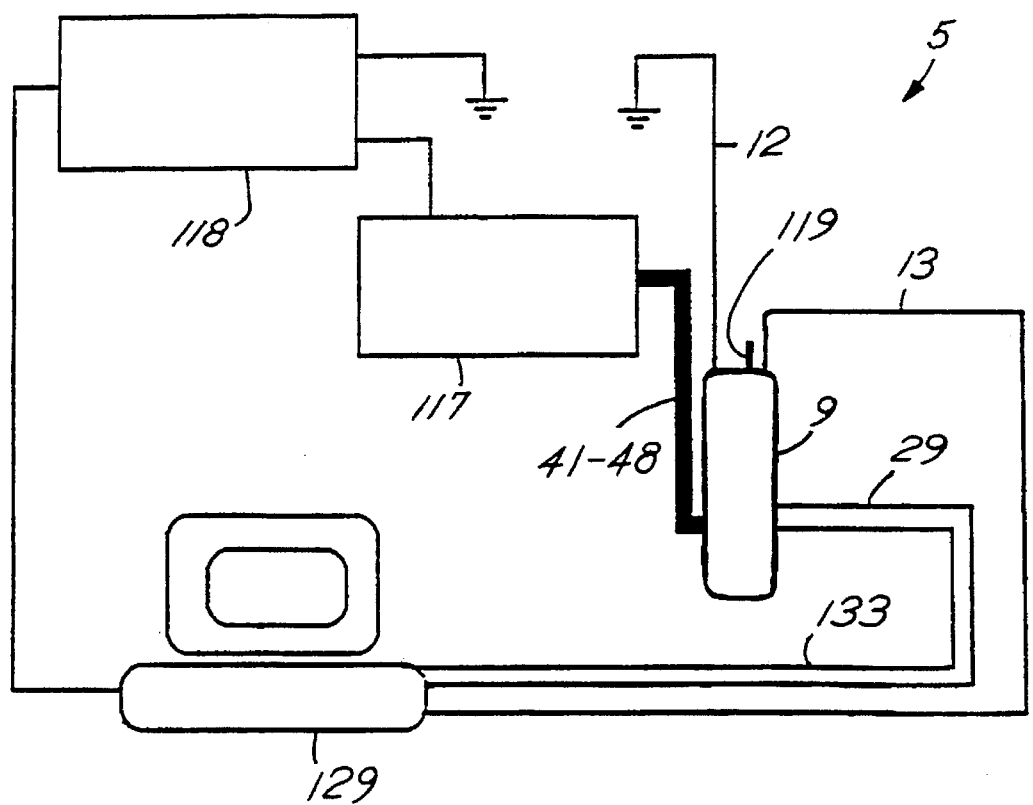
FIG. 17 is a block diagram for the 8-site coulometric feedback device system, showing a modified Threshold Reader, a Threshold Stick, a controlling electrode, a reference electrode, a LAPS contact, a LED control, a computer, an IEEE 488, a Keithley 236 source measure unit, and a Keithley 7001 current switch.
Figure 18:
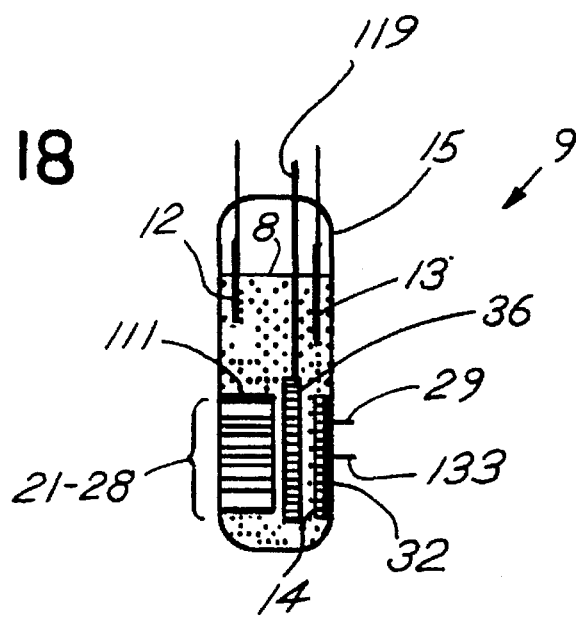
FIG. 18 is a schematic illustration of the modified Threshold Reader identified in FIG. 17, showing a controlling electrode, a reference electrode, a Threshold Stick, a LAPS contact, an LED control, a capture membrane, a feedback electrode array, electrolyte, and plunger/electrodes.

Instrumentation for Supplying Feedback Current to Eight Detection Sites in a Modified Threshold Reader A block diagram of the preferred coulometric feedback system is shown in FIGS. 17 and 18. A modified Threshold® System, employing a modified Threshold Reader Chamber together with a special electronic board 130 (modified board) and software, measures the redox potential and calculates the required feedback current. The modified Threshold workstation may be placed in a noise-shielded box (not shown). The feedback current is applied to the appropriate feedback electrode 21–28 in the feedback electrode array 30 in order to maintain the redox potential constant.

An 8-site coulometric feedback system was constructed and tested for sensitivity, precision, and dynamic range of enzyme detection. The system includes a Keithley 7001 High Density Current Switching System 117 to multiplex the current from a Keithley 236 Source Measure Unit 118 sequentially to individual electrodes 21–28 of a feedback electrode array 30. This current switching system 117 is controlled by a Keithley 7058 Low Current Scanner Card in a 486-type personal computer 129. The switching system 117 is synchronized with, and reports to, a modified MDC50 Card 130, also in the computer 129. The MDC50 Card (not shown) operates the LAPS device 32 and collects LAPS data. Both the scanner card associated with switching system 117, and the MDC50 board, are controlled by a program which runs under Microsoft DOS. LED control line 133 leads from an LED control circuit in computer 129 to LEDs 61–68 adjacent to the modified Threshold Reader chamber 9.

Algorithm for Supplying Feedback Charge to Eight Detection Sites

Enzyme activity of biotinylated β-D-galactosidase (β-gal) was quantitated in initial feasibility studies employing coulometric feedback. Quantitation of ⊖-gal was performed by relating the total feedback charge delivered, over a 216 second quantitation period, to the number of molecules of β-gal present at a detection site on a capture membrane 36. The capture membranes 36, coated with biotinylated BSA, were soaked in the coulometric feedback redox buffer solution (without the substrate) for 30 minutes before capture of β-gal by filtration in order to remove any extraneous redox-active substances from the membranes 36.

An excess of streptavidin is first complexed to β-gal to promote its capture on the biotinyated capture membrane 36, as described previously. The capture procedure is carried out by flowing 100 μl of the streptavidin-biotinylated-β-gal complex through the membrane 36 at a rate of 100 μl/min. Next, the redox LAPS readings are begun in the coulometric feedback Reader Assembly 9 (with the plunger 111 up and without the capture membrane 36). To start the enzyme reaction 150 μl , of coulometric feedback β-gal substrate reagent is flowed through the membrane at a rate of 500 μl/min. The membranes 36 then are immediately inserted into the coulometric feedback Reader Assembly 9 which also contains an excess of coulometric-feedback β-gal substrate reagent. A computer algorithm calculates a set point, for each analysis site, as the average of the ten most recent LAPS redox potential determinations for that site (made at 4.8 second intervals) prior to depressing the plunger 111. Two additional intervals are allowed to pass after the plunger 111 is depressed before a coulometric feedback algorithm is activated to deliver feedback current to the sensing sites. The total feedback charge delivered during a 216 second period is determined for each analysis site.

The coulometric feedback algorithm delivers a pulse of charge (current)×(time) which is intended to maintain a constant steady-state redox potential. The algorithm for feedback charge is given as, $$q = Ad^x \qquad [18]$$

where q is the feedback charge, d is the potential difference between the determined redox potential and the set point, A is a constant with units of amperes·volts$^{-x}$ and x is a unitless constant. Unless otherwise indicated, the value of x was 1.8 and the value of A was $0.6 \times 10^{-5}$ amperes·volts$^{-1.8}$. The maximum and minimum current values employed was $10^{-4}$ and $10^{-6}$ amperes, respectively. The maximum and minimum current pulse widths were 600 and 6 milliseconds, respectively. Thus, a $10^4$ dynamic range of the charge delivered per pulse is achieved. During the 216 second assay period, the number of feedback pulses may be zero or any number from 1 to 15. Thus, in combination, the total dynamic range of the feedback system is $1.5 \times 10^5$.

In operation the feedback charge algorithm specifies that the 600 msec maximum pulse width of is used at all current values until the minimum value of $10^{-6}$ amperes is reached. In order to deliver less charge per pulse, the algorithm then reduces the pulse width until the minimum pulse width of 6 milliseconds is reached. More dynamic range, if needed, could be obtained most easily by selecting the minimum current to less than $10^{-6}$ amperes. (The Keithley 236 Source Measure Unit 118 has an operating range of over 12 logs, i.e. between 1 and $10^{-12}$ amperes.)

Redox Buffer Capacity of Nitrocellulose Immuno-Capture Membrane Surfaces

Figure 10:
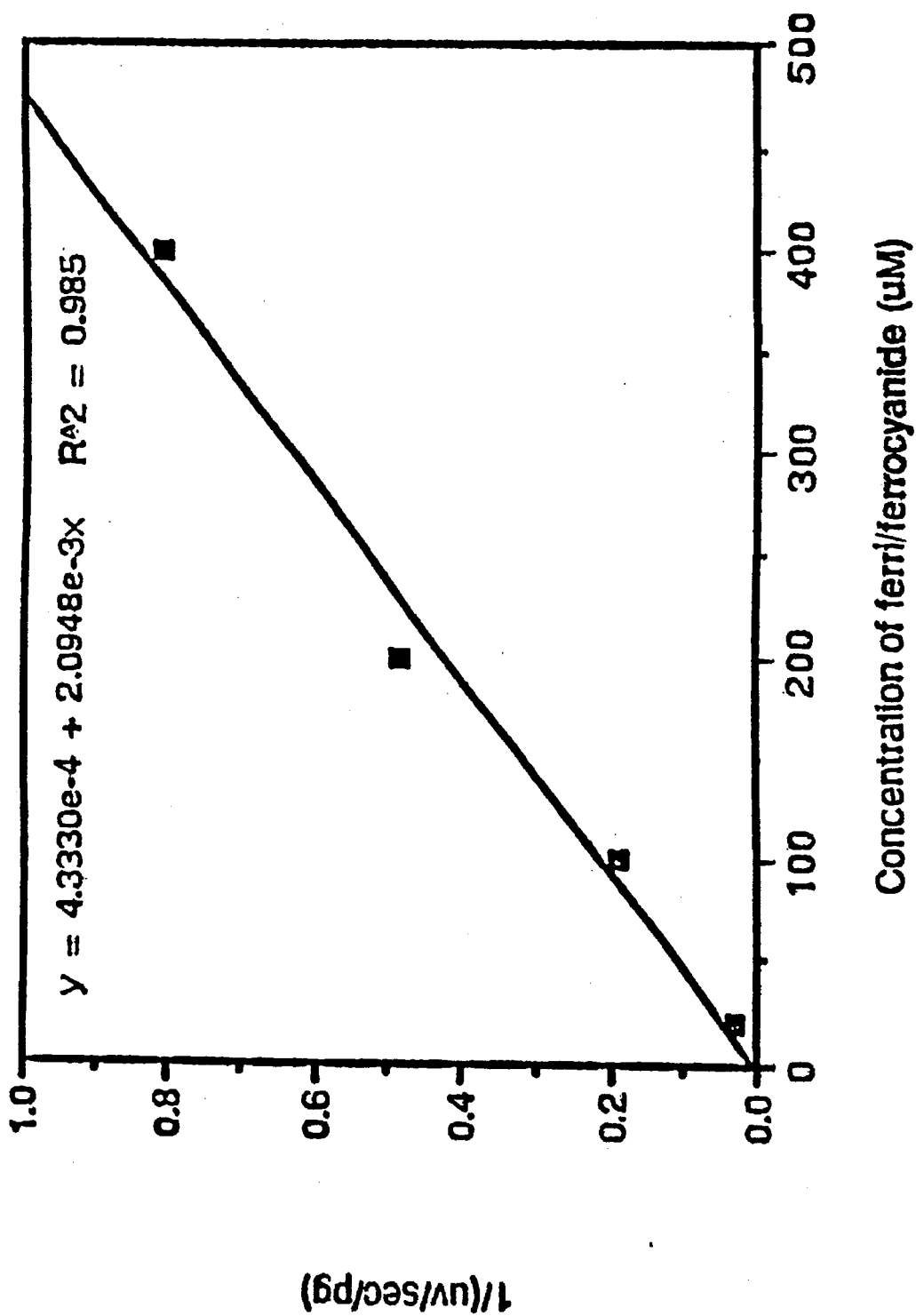
FIG. 10 is a graph plotting the inverse rate of redox potential change versus redox buffer capacity given as the concentration of $Fe(CN)_6^{-3}$ and $Fe(CN)_6^{-4}$(1:1)for the reaction catalyzed by biotin β-D-galactosidase.

We measured the redox buffer capacity of the nitrocellulose immuno-capture membrane 36 by a method similar to that employed previously to measure pH buffer capacity of the same membrane 36. This method entails measuring the rate of potential change caused by a given amount of enzyme captured on the membrane 36 at several different values of volumetric buffering capacity. Extrapolation of the reciprocal of these rates to zero volumetric buffer capacity yields the surface buffering capacity of the membrane 36. FIG. 10 plots the results of such a measurement with a constant amount of biotinylated β-D-galactosidase (β-gal) bound to the membrane 36. Within the experimental limits of precision, no redox buffer capacity is observed. The precision of this method was about ±50 μM, hence the result shows that the redox buffer capacity of the membrane is less than 50 82 M. In comparison, the value of 2.3 mM was found for equivalent pH-buffer capacity of the same membranes 36. Thus the redox buffer capacity is greater than 50 times less than the equivalent, membrane-bound, pH-buffer capacity. Because it is the surface buffer capacity that limits the sensitivity of detection of membrane-bound enzyme in the Threshold System, greater than a 50-fold increase in sensitivity is expected with redox-based potentiometric detection compared to pH-based potentiometric detection.

Alkaline Phosphatase (ALP) Detection Sensitivity and Standard Curve

Figure 11:
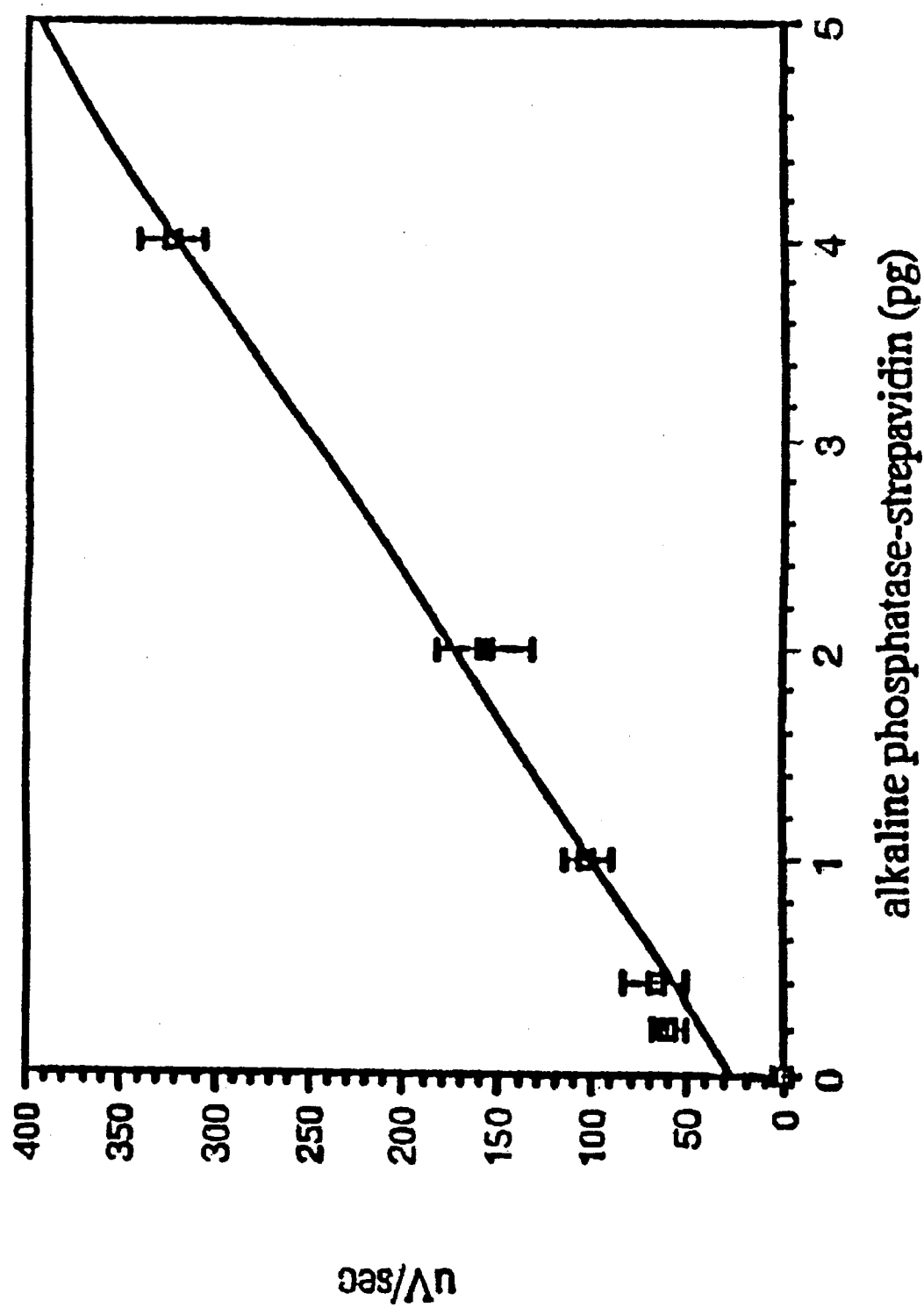
FIG. 11 is a standard curve for the quantitation of streptavidin-alkaline phosphatase.

A typically linear sensor response for detection of streptavidin-alkaline phosphatase is shown in FIG. 11. The slope is 73 μv/sec/pg in the 0.64 μl micro-volume detection chambers 81–88 of the Threshold System. This response was measured at room temperature near 25° C. Increasing the temperature to 37° C. likely would produce a further 2-fold further increase in response.

Comparison of the sensitivity of this method with other methods is shown in Table 1. For example, the slope for detection of the enzyme urease in the pH mode is about 0.5 μv/sec/pg. Therefore, the detection of ALP in the redox detection mode is improved about 150μ-fold over detection of urease in the pH mode. Table 1 further shows that the detection limit (defined as 2 standard deviation units above background) for alkaline phosphatase with this method is 0.2 pg, corresponding to around 650,000 molecules per assay. In contrast the limit of detection of urease, in the pH detection mode, is 69,380,000 molecules. Thus, this redox detection method for ALP has about 100-fold higher detection sensitivity compared to urease detection on a molecular level.

Horseradish Peroxidase (HRP) Detection Sensitivity and Standard Curve

Figure 12:
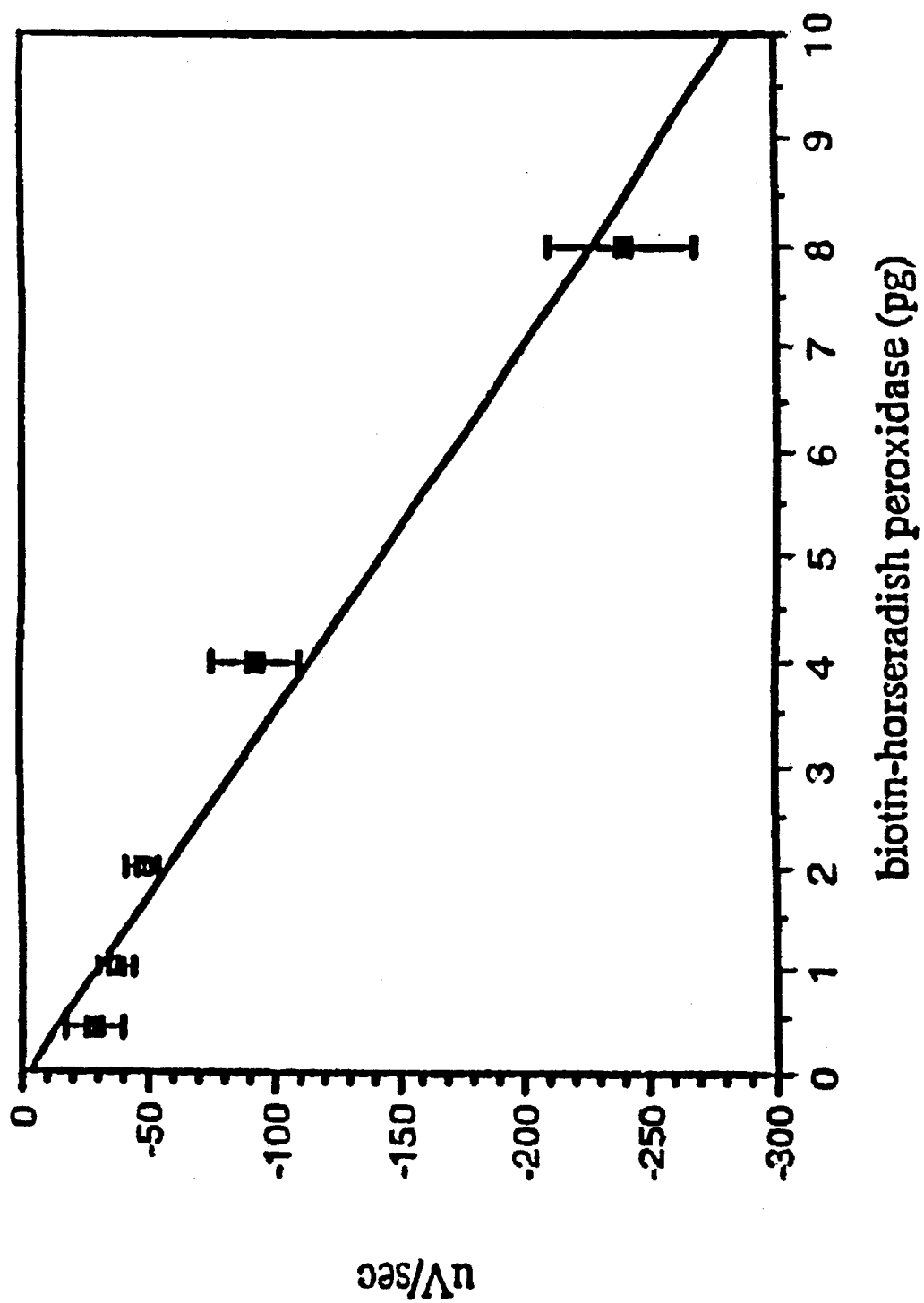
FIG. 12 is a standard curve for the quantitation of biotinylated horseradish peroxidase.

FIG. 12 shows the standard curve of various quantities of biotinylated HRP at pH 5.5, 25° C. The measured detection limit of HRP is 0.4 pg., corresponding to 6.0 million molecules (see Table 1 ).

The plot shown in FIG. 10 demonstrates, for example, that the amount of feedback charge that must be delivered to a particular microvolume site to maintain a substantially constant LAPS-measured potential is directly proportional to the amount of HRP provided on a nitrocellulose membrane 36 at the microvolume site 81–88. Quantitation of the amount of feedback necessary to maintain the substantially constant redox potential condition is thereby shown to be useful in determining the amount of biochemical agents present. The steady-state current necessary to maintain a constant redox potential is directly proportional to the amount of enzyme present.

β-D-galactosidase (β-gal) Detection Sensitivity and Standard Curve

Figure 13:
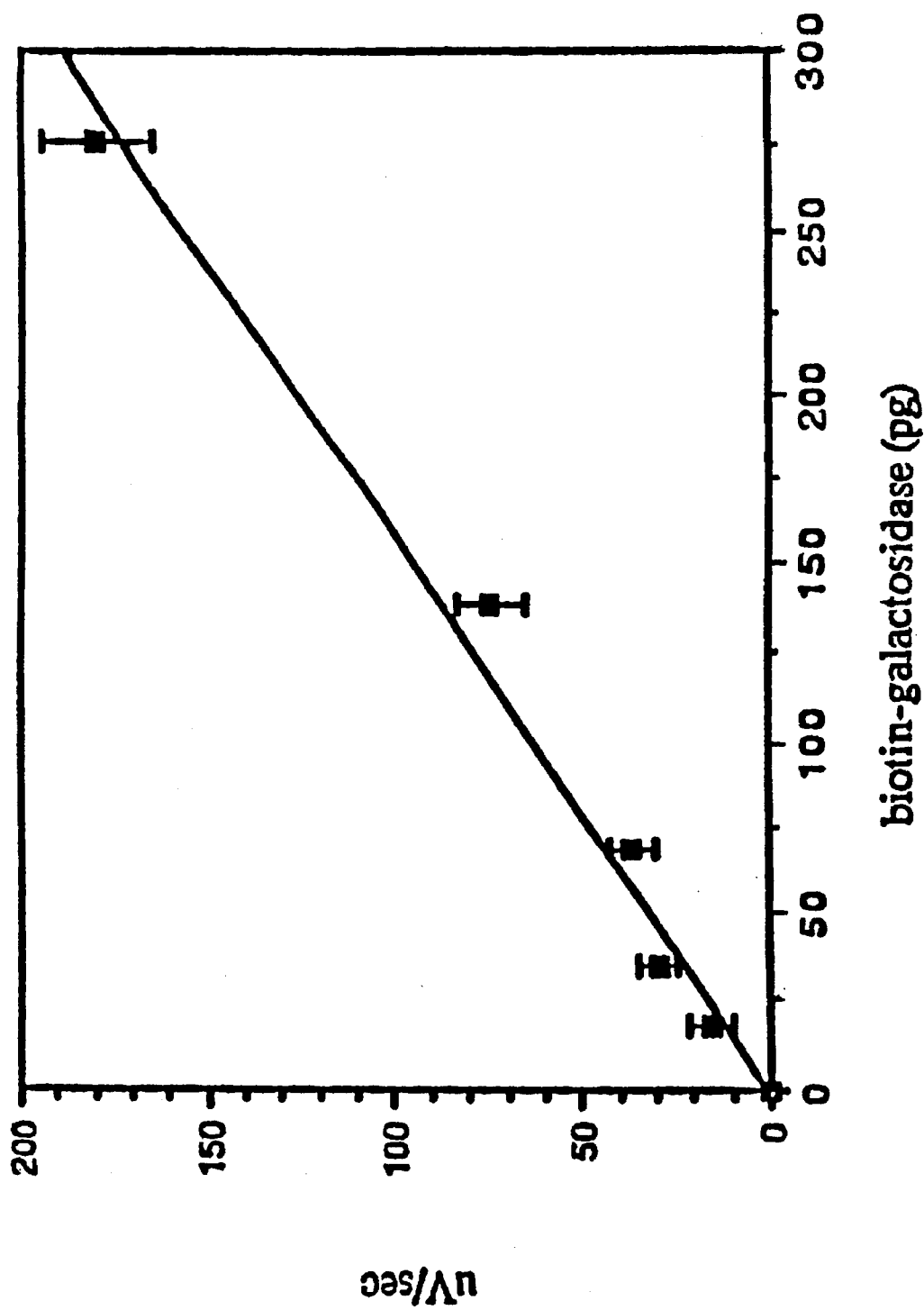
FIG. 13 is a standard curve for the quantitation of biotinylated β-D-galactosidase.

A typical standard curve for quantitation of β-gal is shown in FIG. 13. Experiments with β-gal gave a detection limit of 3 pg., corresponding to 3.4 million molecules (see Table 1 ). This sensitivity, however, may be further increased by determination of substrate $K_m$, optimal pH, concentration of surfactant or concentration of $MgCl_2$. Similar to the reactions catalyzed by ALP and HRP, the initial rate of change in redox potential is directly proportional to the amount of β-gal present.

Glucose Oxidase (GO) Standard Curve and Sensitivity of Detection

Figure 14:
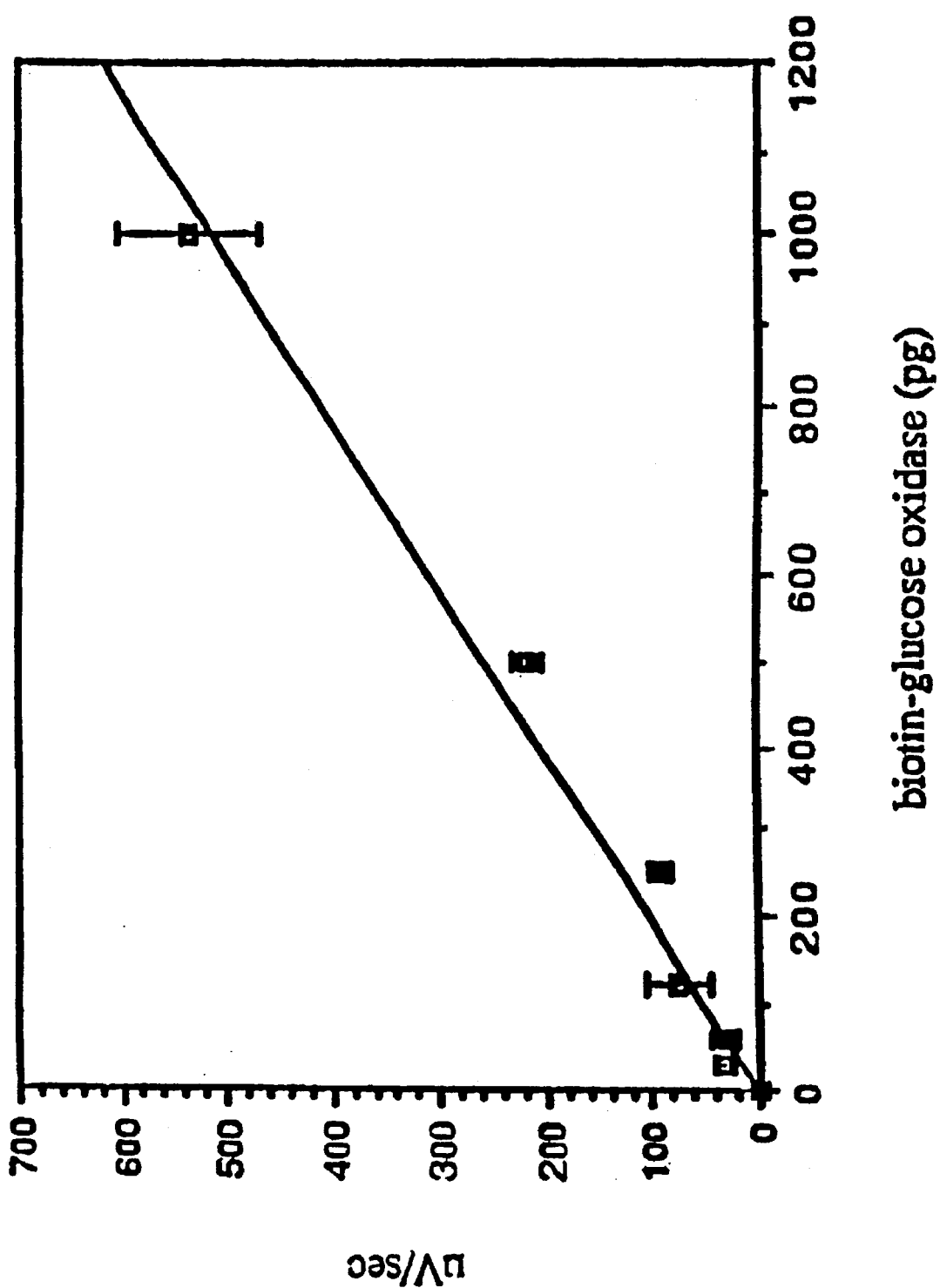
FIG. 14 is a standard curve for the quantitation of biotinylated glucose oxidase.

A typical standard curve for quantitation of biotin glucose oxidase is shown in FIG. 14. Similar to the reactions catalyzed by ALP and HRP and β-gal, the initial rate of change in redox potential is directly proportional to the amount of GO present. Experiments with GO gave a detection limit of 30 pg., corresponding to 90 million molecules (see Table 1 ). The detection system for GO, therefore is roughly equivalent in sensitivity to detection of urease n the pH mode. The sensitivity of the detection system for GO, however, is relatively poor compare to the other redox detection system, namely ALP, HRP and β-gal.

Comparison of pH Mode and Redox Mode Detection in a Model Immunoassay

Figure 15:
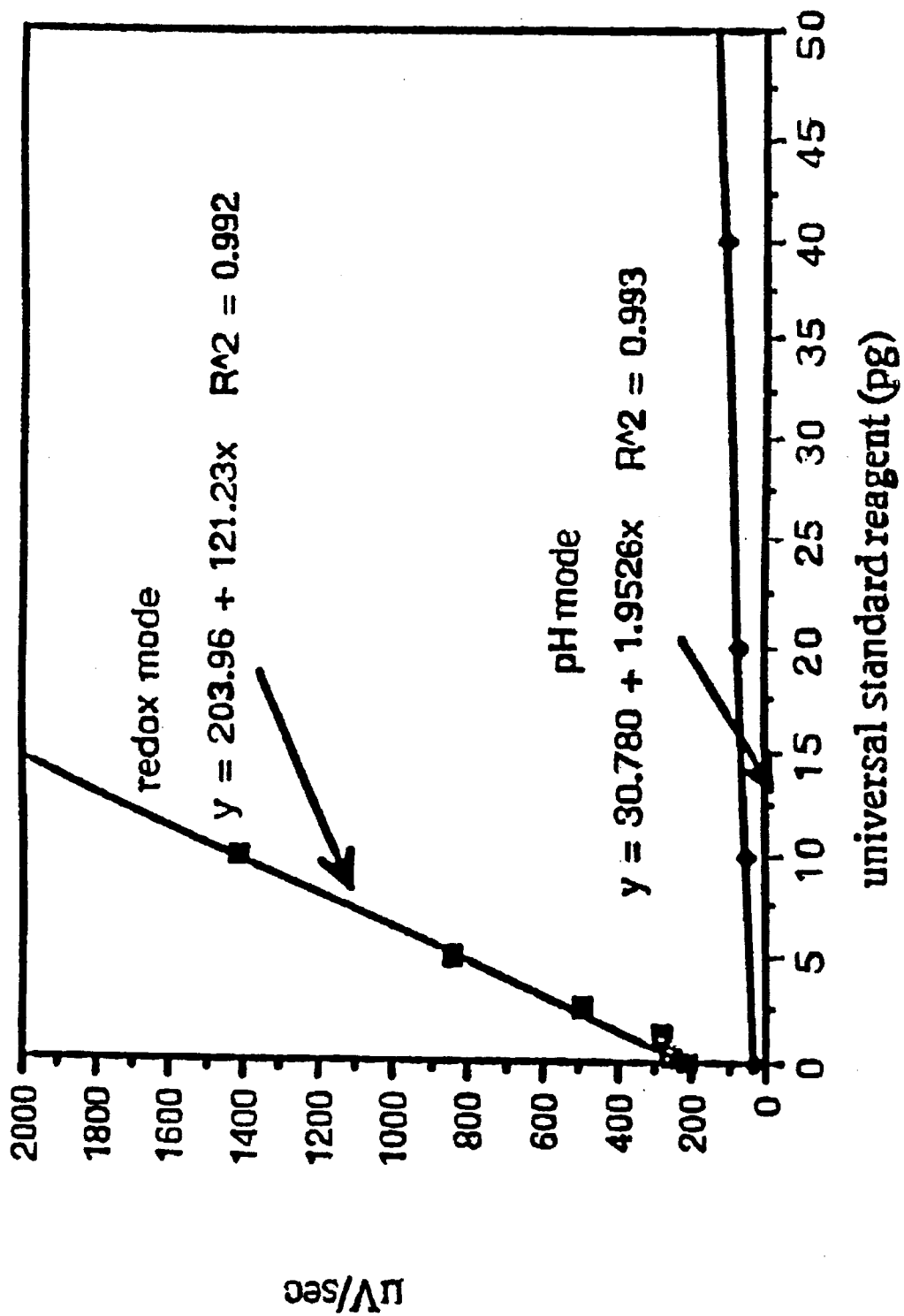
FIG. 15 is a graphical comparison of potentiometric response obtained from the redox mode using alkaline phosphatase conjugate and from the pH mode using urease conjugate.
Figure 16:
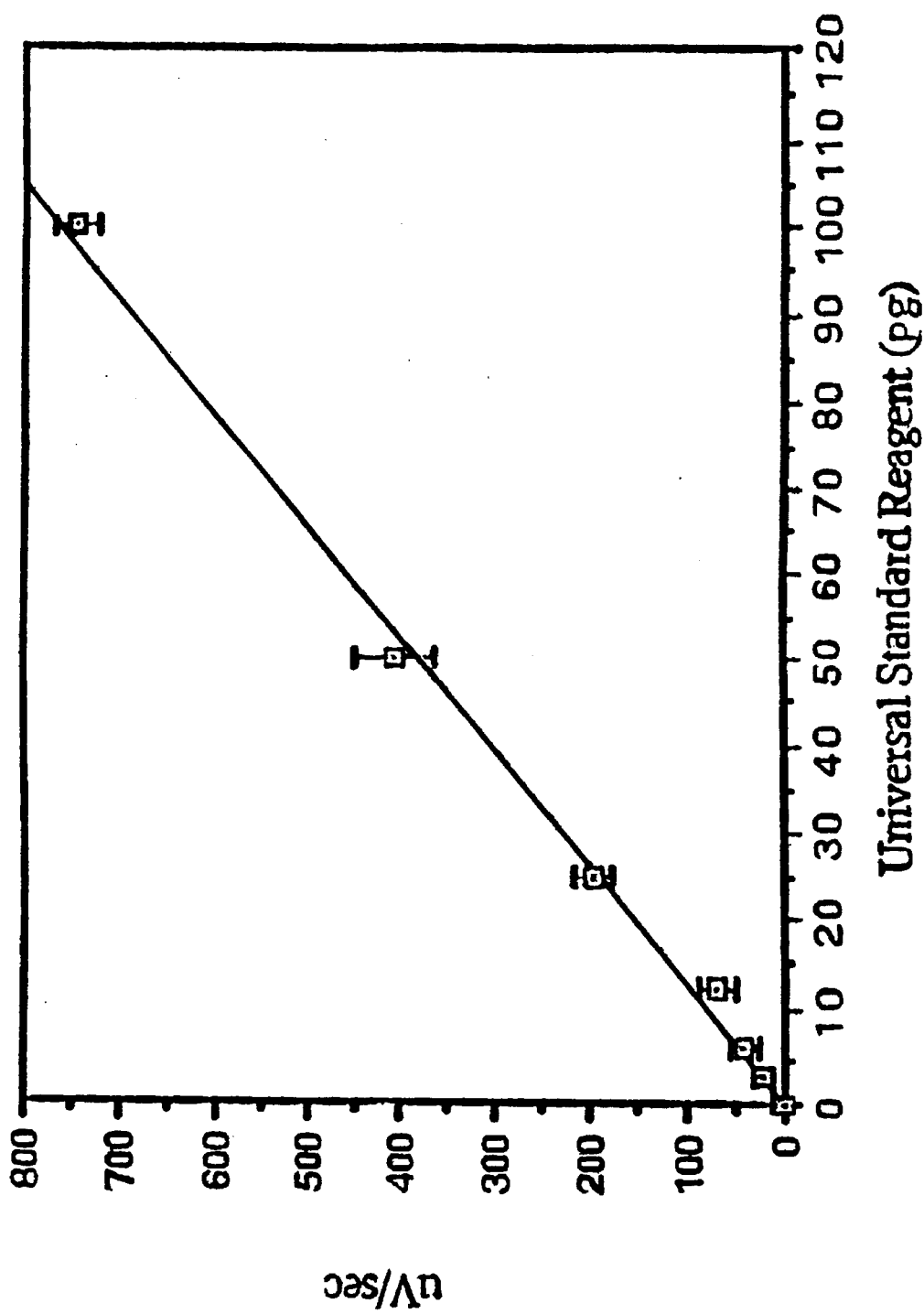
FIG. 16 is a standard curve for the quantitation of biotinylated and fluoresceinated Bovine Serum Albumin (Universal Standard Reagent) using β-D-galactosidase conjugate.

The model analyte employed in a comparative immunoassay was bovine serum albumin conjugated to both biotin and fluorescein. This reagent is called Universal Standard Reagent (USR) and is part of a commercially available ILA™ kit available with the Threshold® System (Molecular Devices Corp.). In the pH detection mode we employed the anti-fluorescein antibody-urease conjugate provided with the ILA™ kit. In the redox detection mode we employed anti-fluorescein antibody conjugates to the immunoassay enzyme labels, ALP, HRP and β-gal. Of the three redox detection systems, the ALP-anti-fluorescein conjugate provided the highest sensitivity for detection of USR. FIG. 15 shows the rate of potential change versus amount of USR when ALP-anti-fluorescein antibody was used in the redox detection mode, and urease-anti-fluorescein antibody was used in the pH detection mode. The rate of potential change for a given amount of universal standard was 60 -fold higher when ALP was used as the enzyme label in the redox detection mode compared to when urease was used as the enzyme label in the pH detection mode. FIG. 16 shows the standard curve detection of USR employing the β-gal-anti-fluorescein antibody in the redox detection mode. Good assay performance and linearity also was observed for this system although the slope of the standard curve (assay gain) was not as good as was observed for the system with the ALP-anti-fluorescein antibody.

Table 2 is a summary of the limits of detection, the slopes of the standard curves (given in molts/second rate per amount of USR) and the rates observed with zero analyte due to nonspecific binding of the anti-fluorescein antibody-enzyme conjugates. The best sensitivity was provided by the ALP-anti-fluorescein conjugate where the detection limit was 0.3 pg USR. This is about a 20-fold improvement in the limit of detection compared to when the urease conjugate was employed in pH detection mode. As mentioned previously, the gain (slope of the standard curve) is increased about 60 times relative to the gain of the pH detection mode employing urease as the enzyme label.

As is also shown in Table 2, the HRP conjugate together with the HRP redox coupling reagents provided a limit of detection of 5 pg USR. This detection limit is about the same as that observed for the urease conjugate in the pH mode measurement. The reason that the HRP system did not give the expected higher sensitivity for detection of USR compared to the urease system appears to be due to a loss of HRP enzyme activity during conjugation of HRP to the anti-fluorescein antibody. Table 1 shows that the gain (slope of standard curves for biotin-HRP detection) to be $1.3\times10^{-6}$ μvolts/sec per molecule of HRP. Table 2 shows that the gain for detection of USR with HRP was only $1.8\times10^{-7}$ μvolts/sec per molecule of USR. This represents only a 7.2% relative efficiency of labeling USR by the antibody-HRP conjugate relative to direct membrane labeling by biotin-HRP. Equivalent comparisons of the urease and ALP systems, in contrast, shows that these systems gave 45% and 57% relative efficiencies of labeling USR by the antibody-enzyme conjugate. The efficiency of labeling by the antibody—β-gal conjugate also was poor. The gain shown in Table 1 for direct membrane labeling by biotin—β-gal is $8.3\times10^{-6}$ μvolts/sec per molecule of biotin—β-gal, whereas the gain shown in Table 2 for labeling USR by the antibody-HRP conjugate is $8.5\times10^{-7}$ μvolts/sec per molecule of USR. This represents a relative efficiency of only 10%. Therefore it appears as if the antibody enzymes conjugation procedure was sub-optimal for HRP and β-gal. Further improvement in the conjugation procedures for these two enzymes should yield up to a 10-fold further improvement in immunoassay gain.

In order to take advantage of all the additional sensitivity of the redox detection systems it is necessary to reduce the nonspecific binding of the antibody-enzyme conjugates to the immuno-capture membrane 36. Table 1 and Table 2 show that the redox detection systems provide enhanced signal levels (gain) for enzyme detection compared to the pH detection system. The last column of Table 2 shows that the Background Signal, which is mainly from nonspecific binding (NSB) of the antibody-enzyme conjugates to the immuno-capture membrane, also is increased in the redox detection systems. In spite of this increased signal from NSB, however, the detection limit for USR was more than 10-fold better with the ALP redox enzyme system compared to the urease pH-detection system. Thus, we have demonstrated an immediate improvement in the sensitivity of detection in a model immunoassay performed with a redox detection system. Further improvement in the sensitivity of detection in redox immunoassays is possible upon reducing NSB.

Testing of the Microfabricated Feedback Electrode Array

Feedback electrode arrays originally constructed of gold in a Macor® insulator base, or gold in a polycarbonate base, were unsatisfactory. These unsatisfactory electrodes had open circuit voltages that typically varied by up to 4 mv across an array of 8 electrodes. Closed circuit current in these unsatisfactory electrode arrays typically varied by about 4 nanoamps continuous current (i.e. 800 nanocoulombs charge over a 200 second immunoassay). This electrode-to-electrode variation severely limited immunoassay sensitivity. This severe limitation required the design and fabrication of high-performance electrode arrays. High performance electrode arrays were constructed on silicon chips by utilizing silicon micro-machining and MOS (metal-oxide-silicon) technology. The details of the fabrication are described above.

Electrochemical performance of each of the electrodes in the array was evaluated in redox buffer solution containing 300 μM ferricyanide and 300 μM ferrocyanide in wash buffer. The open circuit redox potential was measured at various redox buffering capacities (by employing various $K_3Fe(CN)_6/K_4Fe(CN)_6$ ratios). Closed circuit currents, measured with a Princeton Applied Research Model 363 Potentiostat in the potentiostat mode, were recorded for each of the 8 electrodes 90 seconds after setting the potential of each electrode to 217.4 mv versus Ag/AgCl. These measurements were made after the following treatments. First we applied a relatively high current (10 μA) through the individual feedback electrodes 21–28 continuously for 5 minutes. Next, the plunger 111 bearing the feedback electrode array 30 was moved up and down 100 cycles in the redox buffer solution. Finally, the plunger 111 with the feedback electrode array 30 was soaked in redox solution for 3 days. Table 3 shows the redox potentials and closed circuit currents for all 8 feedback electrode sites 21–28. The redox potentials for the 8 electrodes in the array were within 0.4 millivolts. The closed circuit currents varied by 0.4 nanoamps (from 0.4 to 0.8 nA). These results are approximately a 10-fold reduction in variability compared to the previous feedback electrode technology (4 millivolts and 4 nanoamps).

Detection of β-D-Galactosidase with Coulometric Feedback System

Figure 19:
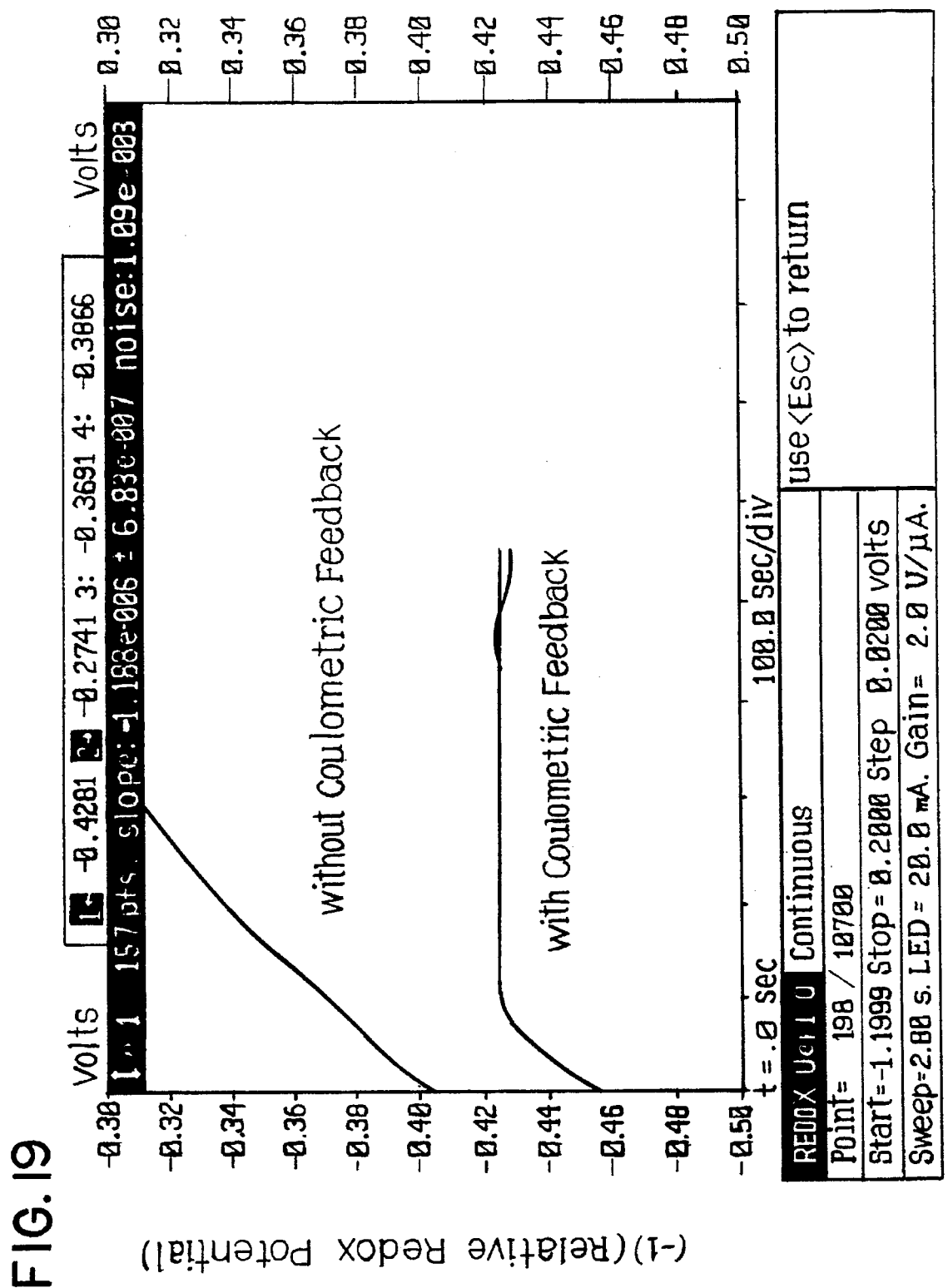
FIG. 19 shows the reference electrode potential relative to the redox potential (as measured by the redox LAPS) plotted as a function of time after immersion of a 100 micron thick immunocapture membrane (with 138 picograms of bound biotinylated β-D-galactosidase) into electrolyte with β-D-galactosidase substrate and 10μM ferricyanide & 10μM ferrocyanide, wherein the top trace shows the response without coulometric feedback and the bottom trace shows the response of an equivalent site having coulometric feedback, and wherein the feedback current was provided with a single-site coulometric feedback which applied a feedback current according to a proportional control algorithm.
Figure 20:
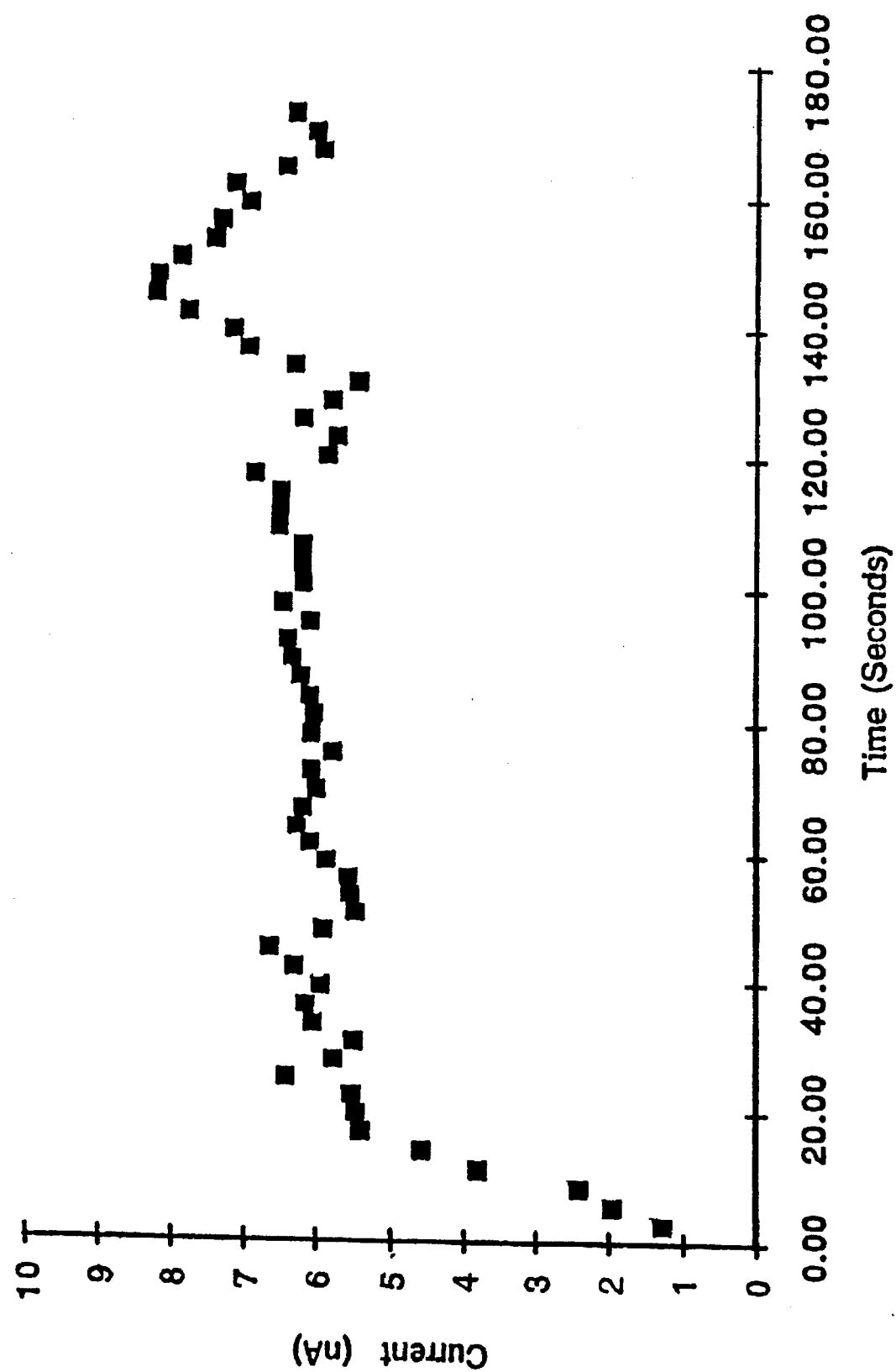
FIG. 20 is a plot of the feedback current injected by the single site coulometric feedback versus time after turning on the control algorithm, wherein the data was collected from the same experiment represented by FIG. 19.

FIG. 19 shows the redox potential response of the LAPS measurement system to 138 picograms of biotinylated β-D-galactosidase immobilized in the detection sites of a Threshold® Stick 119. The electrolyte 8 in the reader contained 5 mM X-Gal, 10 μM $K_4Fe(CN)_6$, 10 μM $K_3Fe(CN)_6$ in wash buffer, pH 7. The redox response is shown both with and without coulometric feedback. Without coulometric feedback, the redox potential increased nearly linearly at a rate of about 340 μvolts/sec. At another detection site (with coulometric feedback) the coulometric feedback control algorithm was started 20 seconds after depressing the plunger 111 of the Threshold ® Reader Chamber. (The 20 second delay was employed for test purposes in order to insure that the initial slope of the redox potential was similar to the case without coulometric feedback.) Fifty seconds after turning on the control algorithm, the redox potential stabilized after changing to a 32 mv more negative value. At steady-state, current pulses of about 6 nanoamps were being injected. (The p-gain was set to $1\times10^{-6}$ which delivered current pulses of $1.7\times10^{-7}$ Amps/Volt redox potential change.) A plot of current versus time after turning on the feedback control for this electrode site is shown in FIG. 20. The feedback current remained approximately constant for 500 seconds at which time the experiment was terminated.

Figure 21:
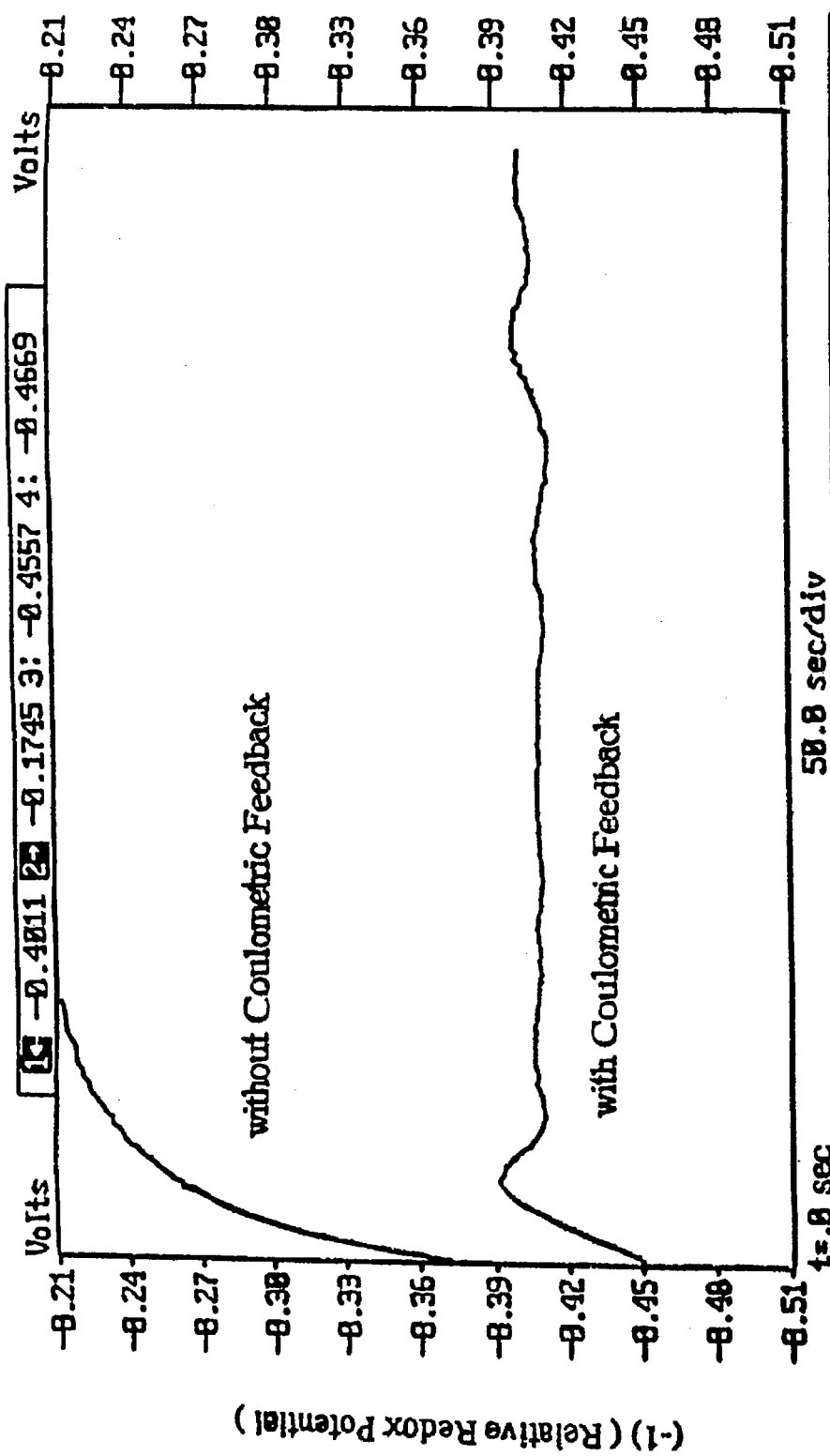
FIG. 21 shows the reference electrode potential relative to the redox potential (as measured by the redox LAPS) plotted as a function of time after immersion of a 100 micron thick immunocapture membrane (with 1380 picograms of bound biotinylated β-D-galactosidase) into electrolyte with β-d-galactosidase substrate and 100μM ferricyanide & 10μM ferrocyanide, wherein the top trace shows the response without coulometric feedback and the bottom trace shows the response of an equivalent site having coulometric feedback, and wherein the feedback current was provided with a single-site coulometric feedback which applied a feedback current according to a proportional control algorithm.
Figure 22:
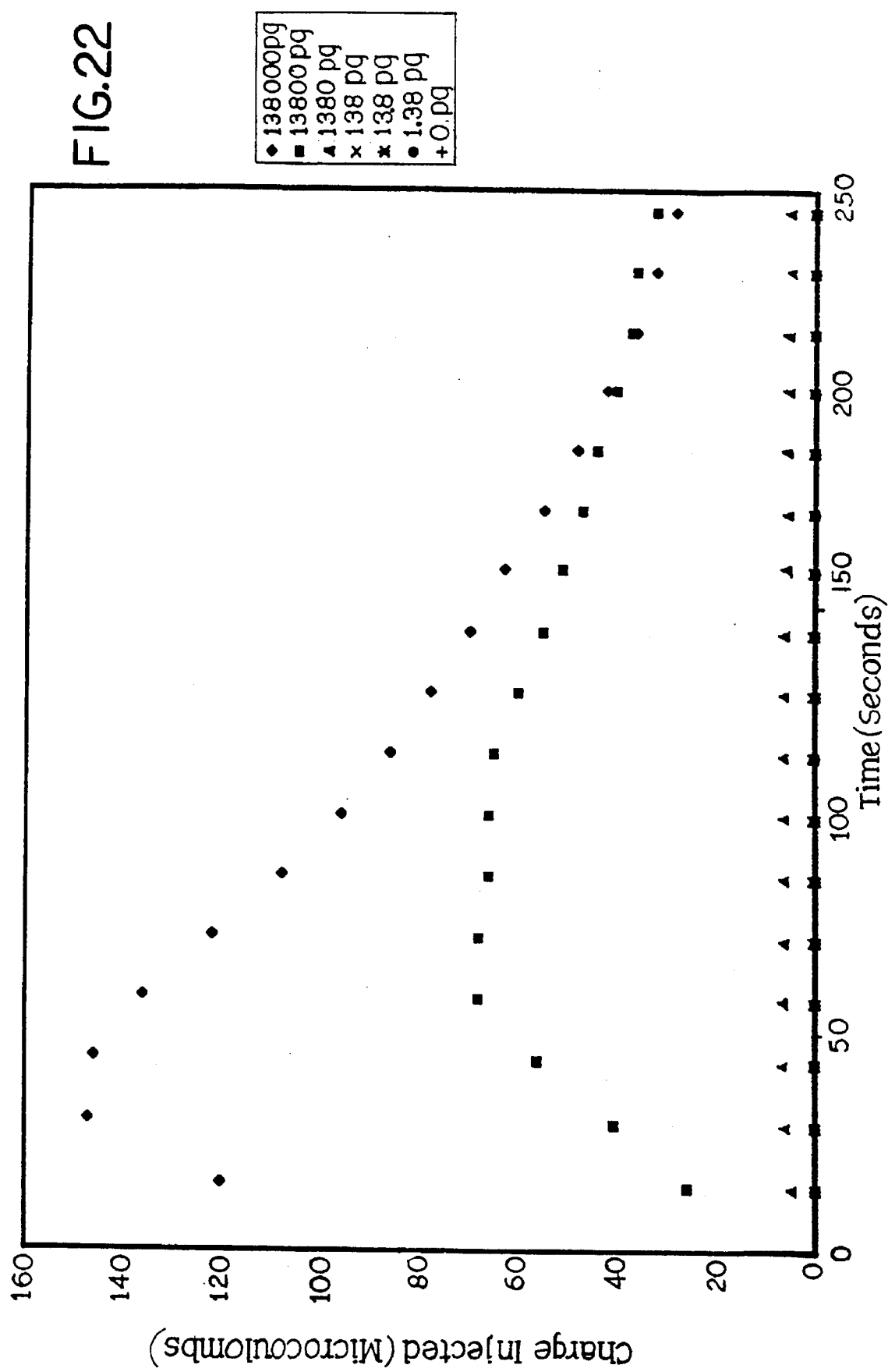
FIG. 22 is a plot of the cumulative charge injected by the 8 site coulometric feedback system versus time after turning on the control algorithm.

FIG. 21 shows the results of an experiment similar to that shown in FIG. 19. The electrolyte, in this case however, contained 10 μM $K_4Fe(CN)_6$ and 100 μM $K_3Fe(CN)_6$ instead of the 10 μM concentration of both redox mediator species employed previously for the experiment shown in FIG. 19. The higher concentration of oxidized mediator was employed to detect higher concentrations of enzyme, thereby increasing the dynamic range of this method.

As shown in FIG. 21, without coulometric feedback the rate of redox potential change with this 10:1 ratio of reduced to oxidized redox mediator is highly nonlinear over time. The concentration of mediator initially begins at 10 µM $K_4Fe(CN)_6$ and 100 µM $K_3Fe(CN)_6$ but as the reaction proceeds, the concentrations will approach 60 µM $K_4Fe(CN)_6$ and 60 µM $K_3Fe(CN)_6$ where redox buffering capacity will be at a maximum (and consequently the rate of redox potential change will be at a minimum). With coulometric feedback, however, the redox potential again stabilized, in this case just 20 mv more negative than the potential at which the feedback was turned on. (The p-gain algorithm for these concentrations of redox mediator was set 10 -fold greater, i.e. to a value of $1 \times 10^{-5}$ which delivered current pulses of $1.7 \times 10^{-6}$ Amps/Volt redox potential change.) The results showed that the 100 µM $K_3Fe(CN)_6$ and 10 µM $K_4Fe(CN)_6$ mixture gives a wider dynamic range than the and 10 µM $K_3Fe(CN)_6$ and 100 µM $K_4Fe(CN)_6$ mixture. The 1M $K_3Fe(CN)_6$ and 10 µM $K_4Fe(CN)_6$ mixture further improves the dynamic range. (This mixture may not be employed in the absence of coulometric feedback because of extreme non-linearity of rate of redox potential change versus time.)

The coulometric feedback method permits determination of enzyme activity with a very wide dynamic range because redox species are regenerated by the feedback electrode. For low redox buffering capacity the ratio of concentrations of oxidized and reduced redox species was selected to be 100:1 (instead of 1:1 for the potentiometric determinations described above). The concentrations of 1M of $K_3Fe(CN)_6$(ferricyanide) and 10 µM $K_4Fe(CN)_6$ (ferrocyanide) were found to be most satisfactory. In this way a very small amount of enzyme causes a large change in the redox potential. High amounts of enzyme, when present, reduce ferricyanide to ferrocyanide thereby driving the ratio toward 1:1, where the buffer capacity is highest, and which is optimal to support highest fluxes of ferrocyanide from enzyme to electrode surfaces.

The dynamic range of this versatile method is very wide, encompassing 5 logs. At the lower end of the range sensitivity is limited by the instrumental noise in determining potential changes and also by the background rates of redox potential changes caused by redox-active impurities on the capture membrane 36. At the lower end of the dynamic range, background signals contribute to the redox potential jumps after closing the plunger 111 and the redox impurities on the membrane 36 interacts with the redox mediators in the solution. The interaction of the impurities on the membrane 36 with the redox mediators is minimized by soaking the membrane 36 in the redox solution for 30 minutes. The average signals without and with the soaking process are 50 µ/sec and 10 µ/sec, respectively. Then, the background signal becomes the jump of the redox potential when closing the plunger 111. By repeating the experiments for fifty times. We found that the jump of the redox potential was a random variation. They jumped between 2 to 10 millivolts and averaged about 5 millivolts. This also results in the high variations of the background signals At the higher end of the range, the maximal amount of enzyme that may be quantitated by the system id determined by the maximum flux of redox species cycling from the enzyme molecules to the surface of the feedback electrode 21–28. The diffusion coefficient of the redox mediators and the thickness of the capture membrane 36 are the major factors which determine the maximum amount of enzyme which may be quantitated. In the coulometric feedback system 5, the greater the activity of enzyme present at a detection site, the higher the current necessary to stabilize the redox potential. Theoretically, the upper limit of the allowed current is determined by the rate of diffusion of $[Fe(CN)_6]^{-4}$ from the enzyme to the feedback electrode surface and the rate of diffusion of $[Fe(CN)_6]^{-3}$ generated at the surface of the feedback electrode 21–28, back to the enzyme. The diffusion limited current is the controlled quantity that represents the maximum rate of conversion. Fick's first law states that the rate of transport (flux), J due to the diffusion is proportional to the concentration gradient.

$$J_x = -D \, dC/dx \quad [19]$$

where D is diffusion coefficient for ferricyanide taken as $6.5 \times 10^{-5}$ cm$^2$/sec (15), C is the concentration of redox mediator, $[Fe(CN)_6]^{-4}$ and $[Fe(CN)_6]^{-3}$, and x is distance perpendicular to the plane of the electrode 21–28. This flux is determined by the thickness of the membrane (100 µm) separating the enzyme and the electrode 21–28, and the concentrations of the redox species. The mean maximum current from the theoretical calculation is 10 µA. The pulse cycle for the current is 0.6 second in 15 seconds. Then, the maximum current injected into the reaction chamber is about 100 µA. This indicates the maximum signal response from the coulometric feedback system 5 that corresponds to the maximum dynamic range at the higher end.

We have set up the experimental condition for the maximum dynamic range. The redox solution consists of 5 mM X-Gal, 10 µ$K_4Fe(CN)_6$, and 1M $K_3Fe(CN)_6$ in wash buffer at room temperature. From 0 pg to 138,000 pg of biotinylated β-galactosidase were immobilized via streptavidin on biotinylated nitrocellulose membranes 36 (Threshold Sticks 119) through the binding mechanism described above. The Threshold Stick 119 was inserted into the Threshold Read Chamber, the plunger 111 having the feedback electrode array 30 was actuated so as to tightly press the membrane 36 between the feedback electrode array 30 and the LAPS electrode 32. The redox potential of each detection site was measured by the LAPS chip 32. The maximum feedback current was set up at 100 µA. And the feedback current required to stabilize the redox potential at each detection site was determined by a software implemented with a PID algorithm. The feedback current was delivered to the opposite side of the membrane 36 for a period of 0.6 seconds in every 15 seconds. For a 100 µm membrane 36, the response time is about 12 seconds to reach the steady state. For the 14.8(4.8 seconds each for 8 different sites) seconds cycle is enough for the experiments. This operation is then repeated for each of the 8 detection sites. When the current injection has been performed at all 8 sites, the redox potential measurements were also repeated until the injected charges is enough to hold the redox potential constant. The currents were recorded and integrated over a total predetermined period, in this case 216 seconds. FIG. 21 shows the cumulative charge of the 8-site coulometric feedback system 5 plotted against time at the condition described above. Total charge injected over this period at a detection sites was directly related to the enzyme activity or amount of enzyme present at this detection site.

We also examined the interference in these experiments. The maximum and minimum currents were 100 µA and 1 µA, respectively at two adjacent detection sites. We found no trace of interference at these two adjacent sites.

Figure 23:
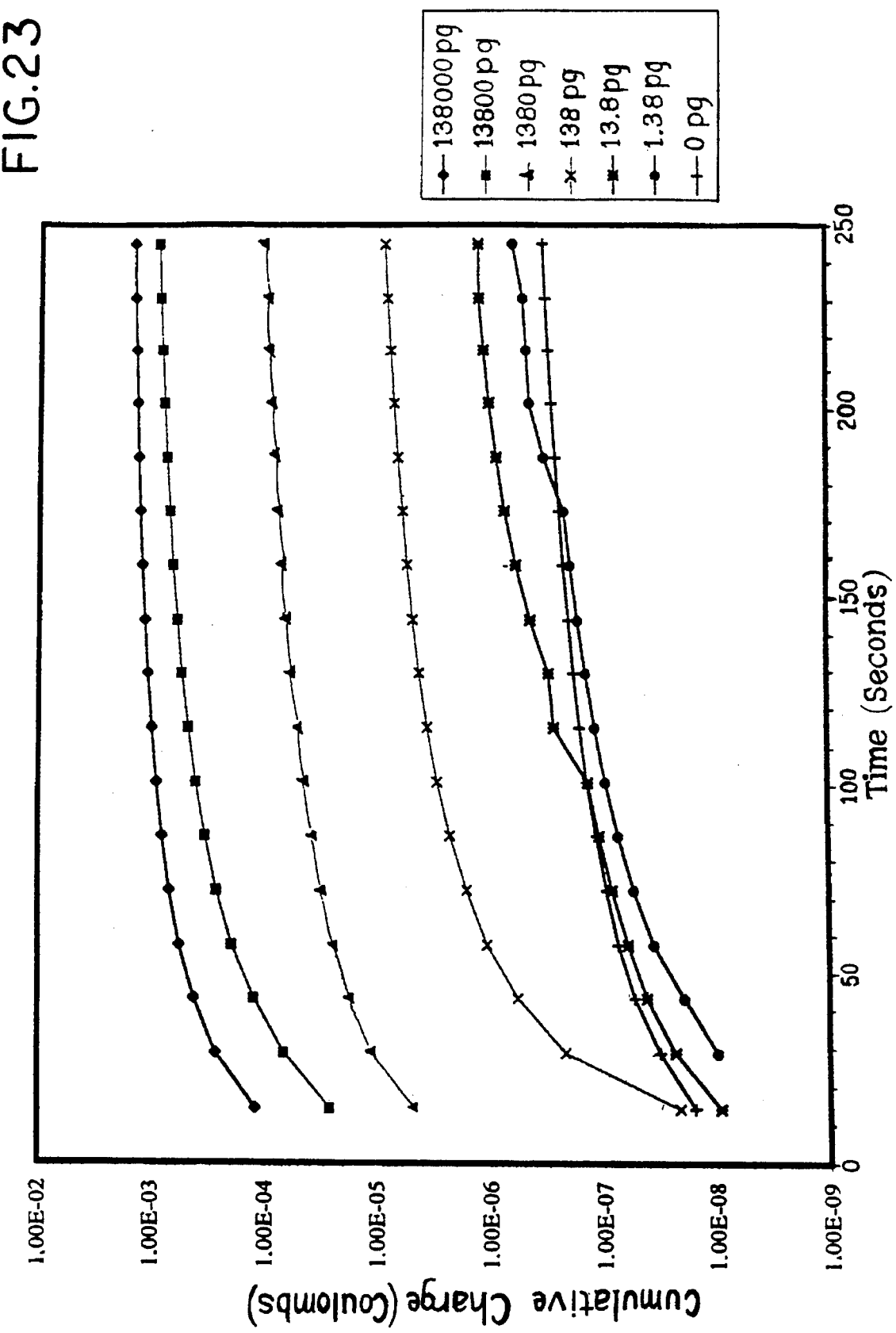
FIG. 23 is a plot of the cumulative charge by the 8 site coulometric feedback system versus time after turning on the control algorithm.
Figure 24:
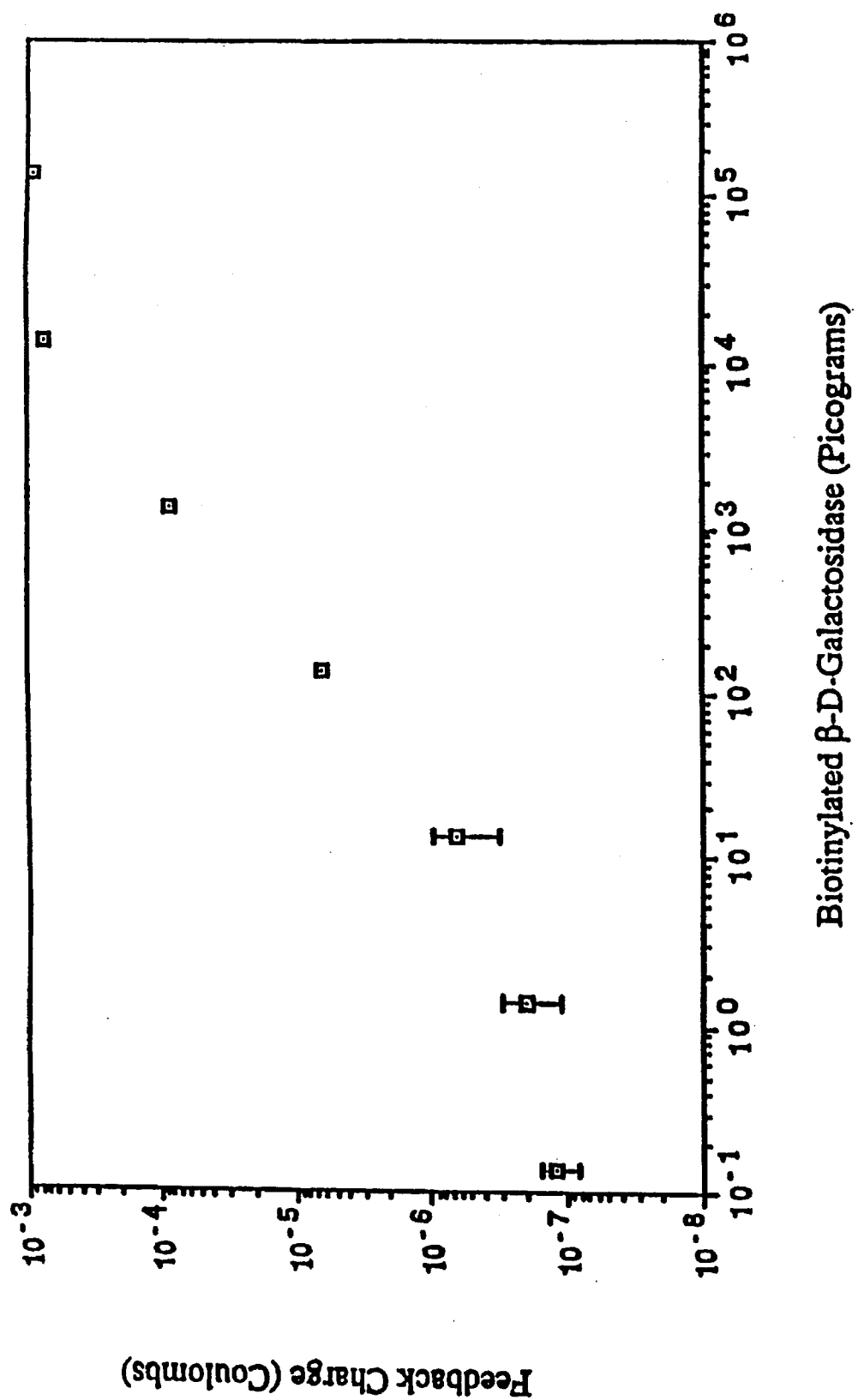
FIG. 24 is a standard curve for quantitation of biotinylated β-D-galactosidase bound on a 100 micron thick immunocapture membrane with the 8 site coulometric feedback device, wherein the redox buffer contained 1M Ferricyanide and 10M Ferrocyanide in Phosphate Buffer Saline (PHS), pH 7, wherein the maximum feedback current was 100μA, and wherein the mean values determined on two different membranes ±SD are shown.

Standard curve for detection of β-D-Galactosidase by using coulometric feedback system A standard curve for detection of β-D-galactosidase was determined with the 8-site coulometric feedback device. The results are shown in FIG. 23. The experiments were carried out on several different nitrocellulose immunocapture membranes 36 to perform this standard curve measurement. The enzyme concentrations were varied from 0.138 pg to 138,000 pg (7 logs of analyte range) on each membrane. The maximum current injected into the reaction chamber 81–88 was fixed at 100 μA per 0.6 second pulse cycle in 15 seconds. The smallest current could be injected into the reaction chamber 81–88 was 1 μA per 6 millisecond pulse cycle in 15 seconds. The reproducibility of the runs repeated at the same condition was acceptable. However, without the proper control of the substrate concentration in the membrane 36 and the right setting of the goal redox potential the data were sometimes inconsistent. Since response signal at the higher end of the standard curve was limited by the substrate concentration, the curve was level off at the higher end. The $K_m$ for the X-gal is about 3 mM. When high enzyme activity was present, the substrate concentration might much lower than the Km value. The enzyme turn over rate was not at its full speed. Then, the rate measured from the redox potential change is much lower than it should be.

At the low end, the standard curve was limited by the background signals. Impurities and the unexpected jump of the redox plunger 111 when closing the plunger 111 were the major contribution to the background signal. This results in the level off the standard curve at the lower end. The random variation of the potential jump due to the plunger pressure described above also caused the high CV% at these concentrations.

The standard curve set forth in FIG. 23 shows the log dependence of the maximum dynamic range of β-D-galactosidase achieved using the coulometric feedback device. In general, there exists an saturation trend in the enzyme activity as the β-D-galactosidase level was increased. It demonstrates approximately 6 log of dynamic range with at least 3 log of the response signals. The minimum detectable enzyme concentration is 1.38 pg.

In short, enzyme substrate and redox mediator systems have been developed to couple label enzymes to a redox-modified light-addressable potentiometric sensor (LAPS). The label enzymes bound to an immunoassay capture membrane 36 were quantitated. This system has been developed for quantitation of four immunoassay label enzymes. The enzymes are alkaline phosphatase, horseradish peroxidase, β-D-galactosidase and glucose oxidase. Each system employs a substrate, having rapid enzymatic turnover and generating a redox-active product, and an oxidized/reduced redox pair (mediator) which couples both to the product of the enzymatic reaction and to the sensing surface of the LAPS detector. Representative standard curves are given for the detection of alkaline phosphatase, β-D-galactosidase, horseradish peroxidase and glucose oxidase. Table 1 is a summary of the limits of detection for each enzyme where the detection limit is defined as the amount of enzyme giving a rate of potential change equal to two times the standard deviation of the background (zero enzyme) rate.

The redox systems provide for rapid, high sensitivity, immunoassays when the redox enzymes are employed as antibody-enzyme labels. A model immunoassay was demonstrated in the redox detection mode and compared to the pH detection mode. The model analyte in the immunoassay was bovine serum albumin derivatized with both biotin and fluorescein (biotin-BSA-fluorescein). The results, summarized in Table 2, show that the detection limit for the model analyte was greater than 10-fold better with the ALP redox enzyme system compared to the, commercially available, urease pH-detection system.

The redox enzyme coupling systems have been designed to work with the coulometric feedback system 5. We have improve the dynamic range of the assay and make assay quantitation insensitive to possible variations in buffer capacity and the volume of the reaction chamber 81–88. To perform ultra-sensitive immunoassay with coulometric feedback reliably, the high quality feedback electrode array 30 was developed using planar semiconductor fabrication technology. Results prove to be satisfactory.

The coulometric feedback system 5 has been validated for 8-site detection of biotinylated β-D-galactosidase bound to commercially-available Threshold® capture membranes 36. Results show that a simple proportional control algorithm is used to supply the feedback current. Analytical results are obtained easily and quickly over a wide dynamic range of from 1 to $10^5$ picograms of β-D-galactosidase enzyme over at least 3 logs of response signal. Experiments designed to examine "cross-talk" between adjacent analysis sites have indicated no interference.

The utility of the coulometric feedback system 5 for quantitation of immunoassays has been demonstrated. Compared to the commercial Threshold® Immunoassay System, the coulometric feedback system approach offers approximately 110-fold improvement both in higher sensitivity and in dynamic range.

TABLE 1

Enzyme Detection Limit (2 Standard Deviation Units above Background) for Streptavidin or Biotinylated Enzymes in Threshold pH and Redox Detection Systems

| Enzyme | Substrate/ (Buffer, pH) Redox Couple | Detection Limit pg (molecules) | Gain uV/sec/pg (uV/sec/molecules) | Background Signal uV/sec |
|---|---|---|---|---|
| Redox Detection: | | | | |
| SA-Alkaline Phosphatase (Mw. 187,000) | BCIP (Tris, pH 10) 200 μM, XTT | 0.2 (650,000) | 73 ($2.3 \times 10^{-5}$) | 82 |
| | BCIP (Tris, pH 8.5) 20 mM Fe(CN)$_6^{3-/4-}$ | 0.2 (650,000) | 28 ($8.7 \times 10^{-6}$) | 75 |
| b-Horseradish Peroxidase (Mw. 40,000) | TMB + H$_2$O$_2$ (Acetate, pH 5.5) + 200 μM Fe(CN)$_6^{3-/4-}$ | 0.4 (6,000,000) | 20 ($1.3 \times 10^{-6}$) | 25 |
| b-βeta-D-Galactosidase (Mw. 540,000) | X-Gal (PBS, pH 7) + 200 μM Fe(CN)$_6^{3-/4-}$ | 3.0 (3,400,000) | 9.3 ($8.3 \times 10^{-6}$) | 30 |
| b-Glucose | Glucose | 30 | 0.5 | 250 |

TABLE 1-continued

Enzyme Detection Limit (2 Standard Deviation Units above Background) for Streptavidin or Biotinylated Enzymes in Threshold pH and Redox Detection Systems

| Enzyme | Substrate/ (Buffer, pH) Redox Couple | Detection Limit pg (molecules) | Gain uV/sec/pg (uV/sec/molecules) | Background Signal uV/sec |
|---|---|---|---|---|
| Oxidase (Mw. 160,000) | (PBS, pH 7) + 200 μM $Fe(CN)_6^{3-/4-}$ + PMS | (90,000,000) | $(1.4 \times 10^{-7})$ | |
| pH Detection: | | | | |
| b-Urease (Mw. 590,000) | Urea (10 mM PBS, pH 7.0) | 68 (69,380,000) | 0.5 $(4.9 \times 10^{-7})$ | 4 |

TABLE 2

Detection Limit (2 Standard Deviation Units above Background) for Bovine Serum Albumin Derivatized with Biotin and Fluorescein (Mw. 66,900) in Threshold pH and Redox Detection Systems

| Enzyme | Substrates | Detection Limit pg (molecules) | Gain uV/sec/pg (uV/sec/molecules) | Background Signal uV/sec |
|---|---|---|---|---|
| Redox Detection: | | | | |
| Alkaline Phosphatase Conjugate | BCIP/XTT (200 μM, pH 10) | 0.3 (2,700,000) | 121 $(1.3 \times 10^{-5})$ | 214 |
| Horseradish Peroxidase Conjugate | TMB + $H_2O_2$ + $Fe(CN)_6^{3-/4-}$ (200 μM, pH 5.5) | 5 (45,000,000) | 1.63 $(1.8 \times 10^{-7})$ | −109 |
| βeta-D-Galactosidase Conjugate | X-Gal (PBS, pH 7) + $Fe(CN)_6^{3-/4-}$ (200 μM) | 4.5 (40,500,000) | 3.27 $(3.6 \times 10^{-7})$ | 217 |
| | X-Gal (PBS, pH 7) + $Fe(CN)_6^{3-/4-}$ (20 μM) | 2.9 (26,100,000) | 7.62 $(8.5 \times 10^{-7})$ | 213 |
| pH Detection: | | | | |
| Urease Conjugate | Urea (in 10 mM PBS) | 5.2 (46,800,000) | 1.95 $(2.2 \times 10^{-7})$ | 33 |

TABLE 3

Open circuit redox potentials and closed circuit currents of the electrodes of a solid-state feedback electrode array. The redox test solution contained 300 μM ferricyanide and 300 μM ferrocyanide in wash buffer.

| Electrode Number | Redox Potential (mv vs. Ag/AgCl) | Current (nanoamps |
|---|---|---|
| 1 | 217.4 | 0.7 |
| 2 | 217.3 | 0.6 |
| 3 | 217.4 | 0.4 |
| 4 | 217.3 | 0.4 |
| 5 | 217.4 | 0.4 |
| 6 | 217.7 | 0.5 |
| 7 | 217.4 | 0.7 |
| 8 | 217.4 | 0.8 |

In closing, it is important to note that it will be readily apparent to those skilled in the art that a number of modifications and changes can be made to the coulometric feedback and system of the present invention without departing from the spirit of the invention. Therefore, the true scope and spirit of this invention are defined by the following claims and their equivalents, to be interpreted in light of the foregoing specification.

What is claimed is:

1. A method for detecting biochemical agents that catalyze a redox potential change comprising the steps of:
   (a) electrochemically contacting an electrolyte containing the biochemical agents with a first electrode and a second electrode;
   (b) measuring a change in the redox potential of the electrolyte through the first electrode;
   (c) delivering coulometric feedback to the electrolyte through the second electrode, in response to a measured change in the redox potential of the electrolyte, in an amount sufficient to maintain the electrolyte at a substantially constant redox potential; and
   (d) quantitizing the amount of coulometric feedback necessary to maintain the electrolyte at the substantially constant redox potential.

2. A method for detecting biochemical agents that catalyze a redox potential change as set forth in claim 1, including the step of electrochemically contacting the electrolyte with a first electrode comprising a metalized sensing region on an insulated surface of a semiconductor.

3. A method for detecting biochemical agents that catalyze a redox potential change as set forth in claim 2, including the steps of applying a bias potential to the semiconductor, illuminating an area on the semiconductor under the metalized sensing region to produce a photocurrent in an external circuit connected to the semiconductor, and measuring the photocurrent to determine the change in redox potential of the electrolyte.

4. A method for detecting biochemical agents that catalyze a redox potential change as set forth in claim 3, including the step of delivering a beam of intensity-modulated light to illuminate the area on the semiconductor.

5. A method for detecting biochemical agents that catalyze a redox potential change as set forth in claim 1, including the step of electrochemically contacting the electrolyte with a carbon sheet electrode as the first electrode.

6. A method for detecting biochemical agents that catalyze a redox potential change as set forth in claim 1, including the step of delivering coulometric feedback to the electrolyte through a current source.

7. A method for detecting biochemical agents that catalyze a redox potential change as set forth in claim 6, including the step of delivering coulometric feedback to the electrolyte through a variable and direct current source.

8. A method for detecting biochemical agents that catalyze a redox potential change comprising the steps of:

(a) electrochemically contacting an electrolyte containing the biochemical agents with an insulated semiconductor having a metalized sensing region;

(b) applying a bias potential to the semiconductor;

(c) illuminating an area on the semiconductor under the metalized sensing region to produce a photocurrent in an external circuit connected to the semiconductor;

(d) measuring the photocurrent;

(e) delivering coulometric feedback to the electrolyte through a controlling electrode, in response to a measured change in the redox potential of the electrolyte, in an amount sufficient to maintain the electrolyte at a substantially constant redox potential; and (f) quantitizing the amount of coulometric feedback necessary to maintain the electrolyte at the substantially constant redox potential.

9. A circuit for detecting biochemical agents that catalyze a redox potential change comprising a first electrode and a second electrode for electrochemical communication with an electrolyte containing the biochemical agents, means operatively associated with the first electrode for measuring a change in redox potential of the electrolyte, and means operatively associated with both the means for measuring a change in redox potential of the electrolyte and the second electrode for delivering coulometric feedback to the electrolyte in response to a measured change in redox potential of the electrolyte.

10. A circuit for detecting biochemical agents that catalyze a redox potential change as set forth in claim 9, wherein the first electrode comprises a metalized sensing region on an insulated surface of a semiconductor.

11. A circuit for detecting biochemical agents that catalyze a redox potential change as set forth in claim 10, wherein the means for measuring a change in redox potential of the electrolyte includes means for applying a bias potential to the semiconductor, means for illuminating an area on the semiconductor under the metalized sensing region to produce a photocurrent in an external circuit connected to the semiconductor, and means for measuring the photocurrent.

12. A circuit for detecting biochemical agents that catalyze a redox potential change as set forth in claim 11, wherein the means for illuminating an area on the semiconductor is a light source that delivers a beam of intensity-modulated light.

13. A circuit for detecting biochemical agents that catalyze a redox potential change as set forth in claim 9, wherein the first electrode is a carbon sheet electrode.

14. A circuit for detecting biochemical agents that catalyze a redox potential change as set forth in claim 9, wherein the means for delivering coulometric feedback to the electrolyte in response to a measured change in redox potential of the electrolyte includes a current source.

15. A circuit for detecting biochemical agents that catalyze a redox potential change as set forth in claim 14, wherein the current source is a variable and direct current source.

16. A circuit for detecting biochemical agents that catalyze a redox potential change as set forth in claim 9, the circuit further comprising means operatively associated with the means for delivering coulometric feedback for quantitating the amount of coulometric feedback delivered to the electrolyte.

17. A circuit for detecting biochemical agents that catalyze a redox potential change comprising a semiconductor, an insulator on at least one surface of the semiconductor to insulate the semiconductor from an aqueous electrolyte containing the biochemical agents, a metalized sensing region on a surface of the insulator for electrochemical communication with the aqueous electrolyte, a controlling electrode for electrochemical communication with the aqueous electrolyte near the metalized sensing region, means for applying a bias potential to the semiconductor, means for illuminating an area on the semiconductor under the metalized sensing region to produce a photocurrent in an external circuit connected to the semiconductor, means for measuring the photocurrent, and means operatively associated with both the means for measuring the photocurrent and the controlling electrode for delivering coulometric feedback to the aqueous electrolyte in response to the measured photocurrent.

18. A circuit for detecting biochemical agents that catalyze a redox potential change as set forth in claim 17, the circuit further comprising means operatively associated with the means for delivering coulometric feedback for quantitating the amount of coulometric feedback delivered to the aqueous electrolyte.

19. A method for detecting biochemical agents that catalyze a redox potential change comprising the steps of:

(a) electrochemically contacting an electrolyte containing the biochemical agents with an electrode; and (b) measuring a steady-state current conducted on the electrode as a result of the redox potential change.

20. A method for detecting biochemical agents that catalyze a redox potential change as set forth in claim 19, including the step of electrochemically contacting the electrolyte with a carbon sheet electrode as the first electrode.

* * * * *